United States Patent
Lyu et al.

(10) Patent No.: US 12,266,116 B2
(45) Date of Patent: Apr. 1, 2025

(54) SYSTEMS AND METHODS FOR IMAGE PROCESSING

(71) Applicant: SHANGHAI UNITED IMAGING HEALTHCARE CO., LTD., Shanghai (CN)

(72) Inventors: Yang Lyu, Shanghai (CN); Chen Xi, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 525 days.

(21) Appl. No.: 17/643,409

(22) Filed: Dec. 8, 2021

(65) Prior Publication Data
US 2022/0108459 A1    Apr. 7, 2022

(30) Foreign Application Priority Data
Dec. 9, 2020 (CN) .......................... 202011428204.7

(51) Int. Cl.
G06T 7/246 (2017.01)
A61B 6/00 (2024.01)

(52) U.S. Cl.
CPC ............ G06T 7/246 (2017.01); *A61B 6/5235* (2013.01)

(58) Field of Classification Search
CPC ........ G46H 30/20; G06H 30/40; G06F 16/51; G06T 7/0014
See application file for complete search history.

(56) References Cited

U.S. PATENT DOCUMENTS

| 7,890,512 B2 * | 2/2011 | Mei .......................... G06F 16/51 382/224 |
| 7,945,078 B2 * | 5/2011 | Sugaya ................... G06F 16/58 382/128 |

(Continued)

FOREIGN PATENT DOCUMENTS

| CN | 110288082 A | 9/2019 |
| CN | 111311704 A | 6/2020 |

(Continued)

OTHER PUBLICATIONS

Xu, Jun, Medical Image Super-resolution Reconstruction Based on Deep Neural Network, Dissertation for the Degree of Master of School of Computer Science and Technology in Shandong University of Finance and Economics, 2019, 66 pages.

(Continued)

*Primary Examiner* — Yosef Kassa
(74) *Attorney, Agent, or Firm* — METIS IP LLC

(57) ABSTRACT

The present disclosure provides a system and method for image reconstruction. The method may include obtaining training samples, the training samples including at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image; and generating a trained image processing model by training a preliminary model using the training samples.

20 Claims, 10 Drawing Sheets

(56) References Cited

U.S. PATENT DOCUMENTS

| | | | |
|---|---|---|---|
| 7,991,232 B2* | 8/2011 | Iwamoto | G06V 10/50 |
| | | | 382/118 |
| 8,335,355 B2* | 12/2012 | Costache | G06F 16/5854 |
| | | | 382/118 |
| 8,879,796 B2* | 11/2014 | Rodriguez Serrano | |
| | | | G06V 10/7715 |
| | | | 382/172 |
| 9,288,376 B2* | 3/2016 | Walker | H04N 1/00204 |
| 9,292,187 B2* | 3/2016 | Whitman | G06F 3/04842 |
| 9,451,899 B2* | 9/2016 | Ritchey | G06T 11/60 |
| 9,769,540 B2* | 9/2017 | Kummer | H04N 21/25891 |
| 10,504,020 B2* | 12/2019 | Trenholm | H04L 67/34 |
| 10,607,090 B2* | 3/2020 | Karlsson | B61L 27/57 |
| 10,902,651 B2* | 1/2021 | Huang | G06N 20/00 |
| 2018/0197317 A1 | 7/2018 | Cheng et al. | |

FOREIGN PATENT DOCUMENTS

| | | |
|---|---|---|
| CN | 111462264 A | 7/2020 |
| CN | 111476283 A | 7/2020 |
| CN | 111626964 A | 9/2020 |
| CN | 111753862 A | 10/2020 |
| CN | 111860588 A | 10/2020 |
| CN | 111915622 A | 11/2020 |
| WO | 2019149718 A1 | 8/2019 |

OTHER PUBLICATIONS

Wang, Yiining et al., Improved Algorithm of Image Super Resolution Based on Residual Neural Network, Journal of Computer Applications, 38(1): 246-254, 2018.

* cited by examiner

600

---

610 — Obtaining training samples, the training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second image and has a higher image quality than the corresponding sample second image 620 — Generating a trained image processing model by training a preliminary neural network model using the plurality groups of training samples in a training process

FIG. 6

SYSTEMS AND METHODS FOR IMAGE PROCESSING

CROSS-REFERENCE TO RELATED APPLICATIONS

This application claims priority of Chinese Patent Application No. 202011428204.7, filed on Dec. 9, 2020, the contents of which are hereby incorporated by reference.

TECHNICAL FIELD

The disclosure generally relates to medical imaging, and more particularly relates to systems and methods for image processing.

BACKGROUND

Emission Computed Tomography (ECT), e.g., Positron emission tomography (PET) and Single-Photon Emission Computed Tomography (SPECT), is a nuclear medicine functional imaging technique that is widely used in medical diagnosis. In ECT, a radioactive substance (i.e., a tracer) is introduced into a subject (e.g., a patient). After metabolism, differences in radioactivity concentration of the tracer are formed in organs of the subject. These differences may be detected and processed by computer for imaging. However, different tracers may correspond to different imaging results. For the technology of reconstructing ECT images using machine learning technology, a large amount of training data is required to generate a high-quality trained model. Generally, a trained model trained using sample images that are generated based on a specific tracer may not be used to process images generated based on other tracers. As a result, for some tracers (e.g., $^{68}$Ga-PSMA) that are not commonly used, it is difficult to obtain sufficient training data to train a model corresponding to these tracers. Therefore, it is desirable to provide systems and methods for training models for processing ECT images generated based on tracers that are commonly used.

SUMMARY

According to an aspect of the present disclosure, a system for model training is provided. The system may include at least one storage device storing a set of instructions, and at least one processor configured to communicate with the at least one storage device. When executing the executable instructions, the at least one processor may be configured to direct the system to perform one or more of the following operations. The system may obtain training samples. The training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image. The system may further generate a trained image processing model by training a preliminary model using the training samples.

In some embodiments, the obtaining the training samples may include obtaining one of the at least one reference first image generated based on first imaging data acquired by an imaging device according to the first tracer; generating the corresponding sample first image by down-sampling the first imaging data; obtaining one of the at least one reference second image generated based on second imaging data acquired by the imaging device according to the second tracer; and generating the corresponding sample second image by down-sampling the second imaging data.

In some embodiments, a first count of the at least one sample first image or the at least one reference first image may be greater than a second count of the at least one sample second image or the at least one reference second image.

In some embodiments, the generating the trained image processing model by training the preliminary model using the training samples may include obtaining a first preliminary weight for each of the at least one sample first image; obtaining a second preliminary weight for each of the at least one sample second image; determining a loss function based on the at least one first preliminary weight and the at least one second preliminary weight; and generating the trained image processing model by training the preliminary model based on the loss function.

In some embodiments, the loss function may include a first term at least related to the at least one first preliminary weight and a second term at least related to the at least one second preliminary weight.

In some embodiments, the at least one second preliminary weight may be greater than the at least one first preliminary weight.

In some embodiments, the training process may include a plurality of iterations. At least one iteration of the plurality of iterations may include determining at least one first prediction output by inputting the at least one sample first image into a first intermediate model, the first intermediate model being the preliminary model in the first iteration of the plurality of iterations, or an updated model generated in a previous iteration; determining at least one second prediction output by inputting the at least one sample second image into the first intermediate model; obtaining at least one first current weight corresponding to the at least one sample first image, and at least one second current weight corresponding to the at least one sample second image, the at least one first current weight being the at least one first preliminary weight in the first iteration of the plurality of iterations, or at least one updated weight corresponding to the at least one first preliminary weight in the previous iteration, the at least one second current weight being the at least one second preliminary weight in the first iteration of the plurality of iterations, or at least one updated weight corresponding to the at least one second preliminary weight in the previous iteration; determining a value of the loss function based on the at least one first current weight, the at least one second current weight, the at least one first prediction output, the at least one reference first image, the at least one second prediction output, and the at least one reference second image; and updating at least one parameter of the first intermediate model based on the value of the loss function.

In some embodiments, the at least one iteration of the plurality of iterations further may include determining a current image difference between the at least one reference second image and the at least one second prediction output; and updating the at least one first current weight and the at least one second current weight based on the current image difference.

In some embodiments, the determining the current image difference between the at least one reference second image and the at least one second prediction output may include determining pixel differences between a plurality of pixels of each of the at least one reference second image and a plurality of pixels of each of the at least one second prediction output; and determining the current image difference based on the pixel differences and the at least one second current weight.

In some embodiments, the updating the at least one first current weight and the at least one second current weight based on the current image difference may include obtaining an initial factor; determining a target factor by comparing the current image difference of the current iteration and a previous image difference that corresponds to the current image difference and is determined in the previous iteration; and updating the at least one first current weight and the at least one second current weight based on the comparison.

In some embodiments, the updating the at least one first current weight and the at least one second current weight based on the comparison may include in response to determining that the current image difference is greater than the previous image difference, decreasing the at least one first current weight; and increasing the at least one second current weight.

In some embodiments, the updating the at least one first current weight and the at least one second current weight based on the comparison may include in response to determining that the current image difference is less than the previous image difference, increasing the at least one first current weight; and decreasing the at least one second current weight.

In some embodiments, the generating the trained image processing model by training the preliminary model using the training samples may include generating a second intermediate model by training the preliminary model using the at least one sample first image and the at least one reference first image; and generating the trained image processing model by training the second intermediate model using the at least one sample second image and the at least one reference second image.

In some embodiments, the generating the trained image processing model by training the second intermediate model using the at least one sample second image and the at least one reference second image may include generating the trained image processing model by iteratively updating parameter values of preset layers in the second intermediate model based on the at least one sample second image and the at least one reference second image.

In some embodiments, there are a threshold count of layers between the preset layers and an output layer of the second intermediate model. The threshold count of layers may be less than 3.

In some embodiments, the trained image processing model may be a trained Feedback Convolutional Neural Network (FB-CNN) including a plurality of sequentially connected subnets. An input of the FB-CNN may be connected to an output of each of the plurality of subnets.

In some embodiments, each of the plurality of subnets may include at least one convolution block, at least one deconvolution block, and a feedback block (FB-block). An output of the FB-block in the subnet may be inputted into a next subnet connected to the subnet. The FB-block may include a plurality of convolutional layers and deconvolutional layers. A portion of the plurality of convolutional layers and deconvolutional layers may be interleaved. Different layers in at least part of the plurality of convolutional layers and deconvolutional layers may be connected to each other.

In some embodiments, the at least one sample first image and the at least one sample second image may serve as inputs for training the preliminary model, and the at least one reference first image and the at least one reference second image may serve as reference outputs for training the preliminary model.

According to another aspect of the present disclosure, a system for image processing is provided. The system may include at least one storage device storing a set of instructions, and at least one processor configured to communicate with the at least one storage device. When executing the executable instructions, the at least one processor may be configured to direct the system to perform one or more of the following operations. The system may obtain an initial image of a subject acquired by an imaging device according to a second tracer. The system may further obtain a trained image processing model. The system may generate a target image by inputting the initial image into the trained image processing model. The target image may have a higher image quality than the initial image. The trained image processing model may be provided by training a preliminary model using training samples. The training samples may include at least one sample first image generated based on a first tracer, at least one reference first image each of which corresponds to one of the at least one sample first image and has a higher image quality than the corresponding sample first image, at least one sample second image generated based on the second tracer different from the first tracer, and at least one reference second image each of which corresponds to one of the at least one sample second image and has a higher image quality than the corresponding sample second image.

According to yet an aspect of the present disclosure, a method for model training is provided. The method may be implemented on a computing device having at least one processor and at least one storage device. The method may include obtaining training samples and generating a trained image processing model by training a preliminary model using the training samples. The training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 6 is a flowchart illustrating an exemplary process for generating a trained image processing model according to some embodiments of the present disclosure;

DETAILED DESCRIPTION

Figure 1:
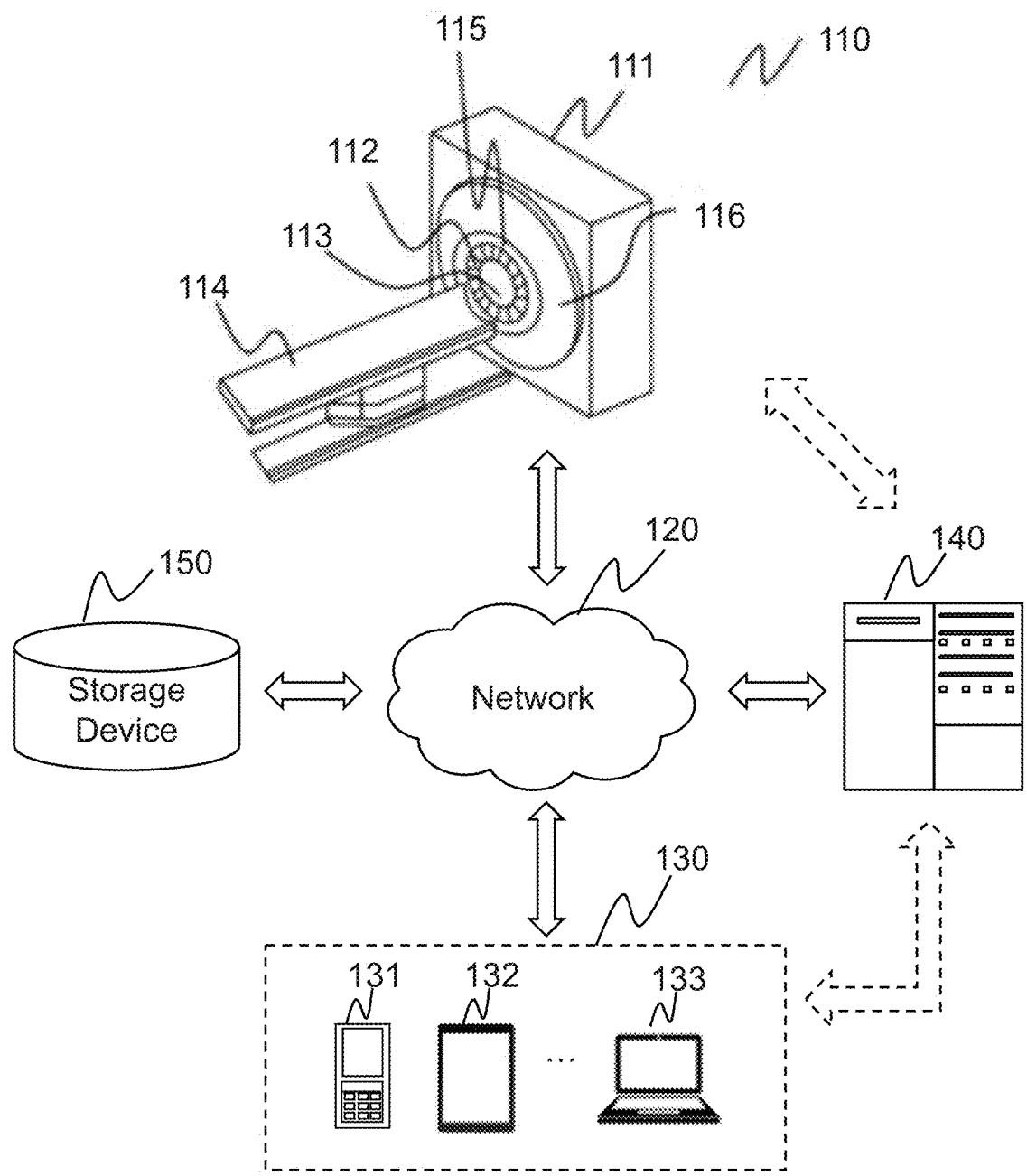
FIG. 1 is a schematic diagram illustrating an exemplary image processing system according to some embodiments of the present disclosure.

The following description is presented to enable any person skilled in the art to make and use the present disclosure and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown but is to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including" when used in this disclosure, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, sections, or assembly of different levels in ascending order. However, the terms may be displaced by another expression if they achieve the same purpose.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage devices. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an erasable programmable read-only memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module, or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

The flowcharts used in the present disclosure illustrate operations that systems implement according to some embodiments in the present disclosure. It is to be expressly understood, the operations of the flowchart may be implemented not in order. Conversely, the operations may be implemented in inverted order, or simultaneously. Moreover, one or more other operations may be added to the flowcharts. One or more operations may be removed from the flowcharts.

The term "image" in the present disclosure is used to collectively refer to image data (e.g., imaging data, projection data) and/or images of various forms, including a two-dimensional (2D) image, a three-dimensional (3D)

image, a four-dimensional (4D), etc. The term "pixel" and "voxel" in the present disclosure are used interchangeably to refer to an element of an image. The term "region," "location," and "area" in the present disclosure may refer to a location of an anatomical structure shown in the image or an actual location of the anatomical structure existing in or on a target subject's body, since the image may indicate the actual location of a certain anatomical structure existing in or on the target subject's body.

In the present disclosure, a representation of a subject (e.g., a patient, a subject, or a portion thereof) in an image may be referred to as "subject" for brevity. For instance, a representation of an organ or tissue (e.g., a heart, a liver, a lung) in an image may be referred to as an organ or tissue for brevity. Further, an image including a representation of a subject may be referred to as an image of a subject or an image including a subject for brevity. Still further, an operation performed on a representation of a subject in an image may be referred to as an operation performed on a subject for brevity. For instance, a segmentation of a portion of an image including a representation of an organ or tissue from the image may be referred to as a segmentation of an organ or tissue for brevity.

In nuclear medical imaging, different tracers may have different imaging mechanisms and may correspond to different imaging results. Generally, a trained image processing model trained using training images generated based on a certain tracer may have a poor performance when processing an image generated based on another tracer. In some occasions, images generated based on the certain tracer may be associated with images generated based on the other tracer. Thus, a specific trained image processing model corresponding to a specific tracer (e.g., a tracer that is not commonly used) may be generated based on a relationship between images corresponding to the specific tracer and the other tracer (e.g., a tracer that is commonly used) according to a transfer learning technique. For example, a difference in imaging mechanism between 2-[$^{18}$F]fluorodeoxyglucose ($^{18}$F-FDG) and $^{68}$Ga-labeled prostate specific membrane antigen ($^{68}$Ga-PSMA) may result in that $^{18}$F-FDG can be taken up in all tissues and/or organs of a subject (e.g., a patient), while $^{68}$Ga-PSMA may be only taken up in a lesion area and tissues and/or organs, such as salivary glands, the liver, kidneys, etc. Thus, the relationship between the corresponding images generated based on $^{18}$F-FDG and $^{68}$Ga-PSMA may be from the whole to the partial, so at least a portion of image information of the images corresponding to $^{18}$F-FDG is associated with the images corresponding to $^{68}$Ga-PSMA. Therefore, the images generated based on $^{18}$F-FDG may be used along with the images generated based on $^{68}$Ga-PSMA to train an image processing model for processing images generated based on $^{68}$Ga-PSMA.

An aspect of the present disclosure relates to systems and methods for model training. For example, the system may obtain training samples. The training samples may include a plurality of sample first images generated based on a first tracer, a plurality of reference first images each of which corresponds to one of the plurality of sample first images and has a higher image quality than the corresponding sample first image, a plurality of sample second images generated based on a second tracer different from the first tracer, and a plurality of reference second images each of which corresponds to one of the plurality of sample second images and has a higher image quality than the corresponding sample second image. The system may further generate a trained image processing model by training a preliminary model using the training samples in a training process. During the training process, the plurality of sample first images and the plurality of sample second images may serve as inputs of the training process, and the plurality of reference first images and the plurality of reference second images may serve as reference outputs of the training process.

In some embodiments, a first count of the plurality of sample first images or the plurality of reference first images may be greater than a second count of the plurality of sample second images or the plurality of reference second images. Accordingly, by training the preliminary model using training samples corresponding to different tracers, even if the training samples corresponding to the second tracer are relatively few, the trained image processing model corresponding to the second tracer may still be generated due to the participation of a large amount of sample data corresponding to the first tracer in the training process, that is, the trained image processing model trained using sample data corresponding to the first tracer and the second tracer can be used to process images generated based on the second tracer. Therefore, it is possible to solve the problem that it is difficult to generate an image processing model for processing images generated based on the second tracer (e.g., a tracer that is not commonly used) due to the scarcity of training samples corresponding to the second tracer.

FIG. 1 is a schematic diagram illustrating an exemplary image processing system according to some embodiments of the present disclosure.

As illustrated in FIG. 1, an image processing system 100 may include an imaging device 110, a network 120, a terminal device 130, a processing device 140, and a storage device 150. The components in the image processing system 100 may be connected in one or more of various ways. Merely by way of example, the imaging device 110 may be connected to the processing device 140 through the network 120. As another example, the imaging device 110 may be connected to the processing device 140 directly as illustrated in FIG. 1. As a further example, the terminal device 130 may be connected to another component of the image processing system 100 (e.g., the processing device 140) via the network 120. As still a further example, the terminal device 130 may be connected to the processing device 140 directly as illustrated by the dotted arrow in FIG. 1. As still a further example, the storage device 150 may be connected to another component of the image processing system 100 (e.g., the processing device 140) directly as illustrated in FIG. 1, or through the network 120.

The imaging device 110 may be configured to acquire imaging data relating to at least part of a subject. The imaging data relating to the at least one part of the subject may include an image (e.g., an image slice), projection data, or a combination thereof. In some embodiments, the imaging data may be a two-dimensional (2D) imaging data, a three-dimensional (3D) imaging data, a four-dimensional (4D) imaging data, or the like, or any combination thereof. The subject may be biological or non-biological. For example, the subject may include a patient, a man-made subject, etc. As another example, the subject may include a specific portion, organ, and/or tissue of the patient. For example, the subject may include the head, the chest, the neck, the thorax, the heart, the stomach, an arm, a palm, a blood vessel, soft tissue, a tumor, nodules, or the like, or any combination thereof. In some embodiments, the imaging device 110 may include a positron emission tomography (PET) device, a single-photon emission computed tomography (SPECT) device, a positron emission tomography-magnetic resonance imaging (PET-MRI) device, a positron emission tomography-computed tomography (PET-CT)

device, a single-photon emission computed tomography-computed tomography (SPECT-CT), or the like, or any combination thereof.

For illustration purposes, a PET device may be taken as an exemplary imaging device 110 in the present disclosure. For example, the PET device may acquire imaging data of a subject after the subject is injected with a tracer (or imaging agent). In some embodiments, according to the principle of action, tracers may be classified into binding tracers, metabolic tracers, blood flow, and blood volume tracers, etc. Exemplary combined tracers may include a monoamine oxidase activity tracer, an adrenergic receptor tracer, an acetylcholinergic receptor tracer, an opioid receptor tracer, an estrogen receptor tracer, a dopamine-system binding tracer, a serotonin-system binding tracer (e.g., a serotonin transporter tracer, a serotonin receptor tracer, etc.), etc. Exemplary metabolic tracers may include an amino acid metabolism tracer (e.g., $^{11}$C-MET, etc.), a fatty acid metabolism tracer (e.g., $^{11}$C-PA, etc.), a nucleic acid metabolism tracer (e.g., $^{11}$C-thymine, etc.), a choline metabolism tracer (e.g., methyl-$^{11}$C choline, etc.), a glucose metabolism tracer (2-$^{18}$F-FDG), a dopamine local metabolism tracer (e.g., 6-$^{18}$F-FDOPA, etc.), etc. Exemplary blood flow and blood volume tracers may include $^{11}$CO, $^{11}$CO$_2$, N-butanol labeled by $^{11}$C, $^{13}$NH$_3$, $^{62}$Cu-PTSM, $^{15}$O$_2$, H$_2$$^{15}$O, etc. In some embodiments, according to the type of radionuclide, the tracers may be classified into a fluorine-18 ($^{18}$F)) labeled tracer, a carbon-11 ($^{11}$C) labeled tracer, a nitrogen-13 ($^{13}$N) labeled tracer, an oxygen-15 ($^{15}$O) labeled tracer, etc. In some embodiments, according to the source of radionuclide, the tracers may be classified into a tracer prepared by a cyclotron, a tracer prepared by a medical accelerator, etc. In some embodiments, according to the target organ, the tracers may be classified, into a tumor tracer, a nerve tracer, a cardiovascular tracer, etc.

In some embodiments, the imaging device 110 may include a supporting assembly 111 (e.g., a gantry), a detector assembly 112, a scanning table 114, an electronic module 115, and a cooling assembly 116.

The supporting assembly 111 may support one or more components of the imaging device 110 including, e.g., the detector assembly 112, the electronic module 115, the cooling assembly 116, etc. In some embodiments, the supporting assembly 111 may include a main gantry, a gantry base, a front cover plate, and a rear cover plate (not shown). The front cover plate may be connected to the gantry base. The front cover plate may be substantially perpendicular to the gantry base. As used herein, "substantially" indicates that a deviation (e.g., a deviation from being perpendicular) is below a threshold. For instance, the deviation of the angle between the front cover plate and the gantry base from 90° may be below a threshold, e.g., 10°, 8°, 5°, etc. The front cover plate may be mounted on the main gantry. The main gantry may include one or more supporting frames to accommodate the detector assembly 112 and/or the electronic module 115. The main gantry may include a substantially circular opening (e.g., a detection region 113) to accommodate a subject for scanning. In some embodiments, the opening of the main gantry may have another shape including, for example, an oval. The rear cover plate may be mounted on the main gantry opposing the front cover plate. The gantry base may support the front cover plate, the main gantry, and/or the rear cover plate. In some embodiments, the imaging device 110 may include a casing configured to cover and protect the main gantry.

The detector assembly 112 may detect radiation events (e.g., gamma photons) emitted from the detection region 113. In some embodiments, the detector assembly 112 may receive radiation rays (e.g., gamma rays) impinging on the detector assembly 112 and generate electrical signals. In some embodiments, the detector assembly 112 may include one or more detector units. The one or more detector units may be packaged to form a detector block. One or more detector blocks may be packaged to form a detector cassette. One or more detector cassettes may be arranged to form a detector module. One or more detector modules may be arranged to form a detector ring.

The electronic module 115 may collect and/or process the electrical signals generated by the detector assembly 112. The electronic module 115 may include an adder, a multiplier, a subtracter, an amplifier, a drive circuit, a differential circuit, an integral circuit, a counter, a filter, an analog-to-digital converter (ADC), a lower limit detection (LLD) circuit, a constant fraction discriminator (CFD) circuit, a time-to-digital converter (TDC), a coincidence circuit, or the like, or any combination thereof. The electronic module 115 may convert an analog signal relating to an energy of radiation rays received by the detector assembly 112 to a digital signal. The electronic module 115 may compare a plurality of digital signals, analyze the plurality of digital signals, and determine imaging data based on the energies of radiation rays received by the detector assembly 112.

Merely by way of example, if the detector assembly 112 is part of a PET scanner that has a large (or long) axial field of view (FOV) (e.g., 0.75 meters to 2 meters long), the electronic module 115 may have a high data input rate from multiple detector channels. The electronic module 115 may collect the electrical signals from the detector assembly 112 through the detector channels. For example, the electronic module 115 may handle up to tens of billion events per second. In some embodiments, the data input rate may relate to a count of detector units in the detector assembly 112.

The cooling assembly 116 may produce, transfer, deliver, channel, or circulate a cooling medium to the imaging device 110 to absorb heat produced by the imaging device 110 during an imaging procedure. In some embodiments, the cooling assembly 116 may be entirely integrated into the imaging device 110 and be a part of the imaging device 110. In some embodiments, the cooling assembly 116 may be partially integrated into the imaging device 110. For example, a portion of the cooling assembly 116 may be integrated into the imaging device 110, while another portion of the cooling assembly 116 may be configured outside the imaging device 110. The cooling assembly 116 may allow the imaging device 110 to maintain a suitable and stable working temperature (e.g., 25° C., 30° C., 35° C., etc.). In some embodiments, the cooling assembly 116 may control the temperature of one or more target components of the imaging device 110. The target components may include the detector assembly 112, the electronic module 115, and/or any other components that generate heat in operation. The cooling medium may be gaseous, liquid (e.g., water), or the like, or any combination thereof. In some embodiments, the gaseous cooling medium may be air.

The network 120 may include any suitable network that can facilitate the exchange of information and/or data for the image processing system 100. In some embodiments, one or more components (e.g., the imaging device 110, the processing device 140, the storage device 150, or the terminal device 130) of the image processing system 100 may communicate information and/or data with one or more other components of the image processing system 100 via the network 120. For example, the processing device 140 may obtain imaging data from the imaging device 110 via the network 120. As another example, the processing device 140 may obtain user instructions from the terminal device 130 via the network 120. In some embodiments, the network 120 may be any type of wired or wireless network, or a combination thereof.

The terminal device 130 may be connected to and/or communicate with the imaging device 110, the processing device 140, and/or the storage device 150. For example, the terminal device 130 may enable user interactions between a user and the image processing system 100. For example, the user may instruct the imaging device 110 to acquire imaging data or instruct the processing device 140 to process images via the terminal device 130. In some embodiments, the terminal device 130 may include a mobile device 131, a tablet computer 132, a laptop computer 133, or the like, or any combination thereof. In some embodiments, the terminal device 130 may be part of the processing device 140.

The processing device 140 may process data and/or information obtained from the imaging device 110, the terminal device 130, and/or the storage device 150. In some embodiments, the processing device 140 may process imaging data obtained from the imaging device 110 or the storage device 150. For example, the processing device 140 may reconstruct a target image of the subject by applying a target reconstruction model. As another example, the processing device 140 may generate the target reconstruction model by training a preliminary model using a plurality of training samples. In some embodiments, the generation and/or updating of the target reconstruction model may be performed on a processing device, while the application of the target reconstruction model may be performed on a different processing device. In some embodiments, the generation of the target reconstruction model may be performed on a processing device of a system different from the image processing system 100 or a server different from a server including the processing device 140 on which the application of the target reconstruction model is performed. For instance, the generation of the target reconstruction model may be performed on a first system of a vendor who provides and/or maintains such a target reconstruction model and/or has access to training samples used to generate the target reconstruction model, while image reconstruction based on the provided target reconstruction model may be performed on a second system of a client of the vendor. In some embodiments, the generation of the target reconstruction model may be performed online in response to a request for image reconstruction. In some embodiments, the generation of the target reconstruction model may be performed offline.

In some embodiments, the target reconstruction model may be generated and/or updated (or maintained) by, e.g., the manufacturer of the imaging device 110 or a vendor. For instance, the manufacturer or the vendor may load the target reconstruction model into the image processing system 100 or a portion thereof (e.g., the processing device 140) before or during the installation of the imaging device 110 and/or the processing device 140, and maintain or update the target reconstruction model from time to time (periodically or not). The maintenance or update may be achieved by installing a program stored on a storage device (e.g., a compact disc, a USB drive, etc.) or retrieved from an external source (e.g., a server maintained by the manufacturer or vendor) via the network 120. The program may include a new model (e.g., a new image reconstruction model) or a portion of a model that substitute or supplement a corresponding portion of the model.

In some embodiments, the processing device 140 may be a single server or a server group, etc. The server group can be centralized or distributed. In some embodiments, the processing device 140 may be local to or remote from the image processing system 100. For example, the processing device 140 may access information and/or data from the imaging device 110, the storage device 150, and/or the terminal device 130 via the network 120. As another example, the processing device 140 may be directly connected to the imaging device 110, the terminal device 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, and inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the imaging device 110, the terminal device 130, and/or the processing device 140. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. In some embodiments, the storage device 150 may be implemented on a cloud platform.

In some embodiments, the storage device 150 may be connected to the network 120 to communicate with one or more other components (e.g., the processing device 140, the terminal device 130) of the image processing system 100. One or more components of the image processing system 100 may access the data or instructions stored in the storage device 150 via the network 120. In some embodiments, the storage device 150 may be part of the processing device 140, or directly or indirectly connected to the processing device 140.

It should be noted that the above description of the image processing system 100 is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure.

Figure 2:
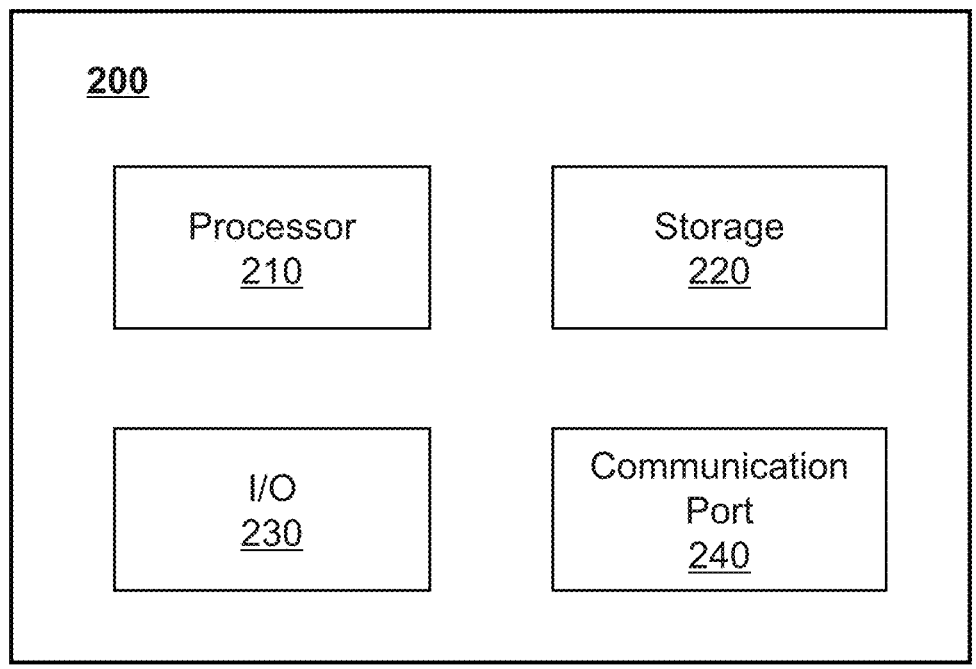
FIG. 2 is a schematic diagram illustrating hardware and/or software components of an exemplary computing device according to some embodiments of the present disclosure.

FIG. 2 is a schematic diagram illustrating hardware and/or software components of an exemplary computing device according to some embodiments of the present disclosure. In some embodiments, a component of the image processing system 100 (e.g., the processing device 140) may be implemented on the computing device 200. As illustrated in FIG. 2, the computing device 200 may include a processor 210, a storage 220, an input/output (I/O) 230, and a communication port 240.

The processor 210 may execute computer instructions (e.g., program codes) and perform functions of the processing device 140 in accordance with techniques described herein. The computer instructions may include, for example, routines, programs, objects, components, data structures, procedures, modules, and functions, which perform particular functions described herein. For example, the processor 210 may process imaging data obtained from the imaging device 110 using a trained image processing model and generate a target image.

Merely for illustration, only one processor is described in the computing device 200. However, it should be noted that the computing device 200 in the present disclosure may also include multiple processors, and thus operations and/or method operations that are performed by one processor as described in the present disclosure may also be jointly or separately performed by the multiple processors.

The storage 220 may store data/information obtained from the imaging device 110, the terminal device 130, the storage device 150, and/or any other component of the image processing system 100. In some embodiments, the storage 220 may store one or more programs and/or instructions to perform exemplary methods described in the present disclosure. For example, the storage 220 may store a program for the processing device 140 to train an image processing model based on training samples.

The I/O 230 may input and/or output signals, data, information, etc. In some embodiments, the I/O 230 may enable a user interaction with the processing device 140. In some embodiments, the I/O 230 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof.

The communication port 240 may be connected to a network (e.g., the network 120) to facilitate data communications. The communication port 240 may establish connections between the processing device 140 and the imaging device 110, the terminal device 130, and/or the storage device 150. The connection may be a wired connection, a wireless connection, any other communication connection that can enable data transmission and/or reception, and/or any combination of these connections.

Figure 3:
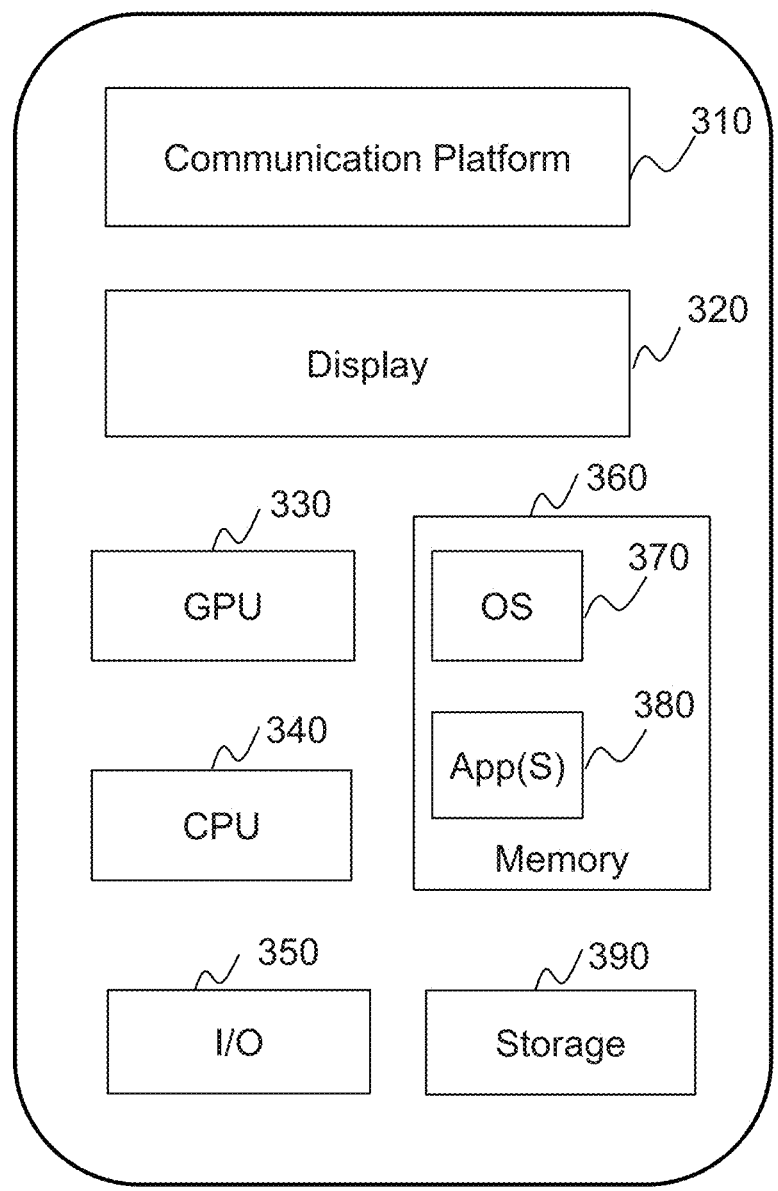
FIG. 3 is a schematic diagram illustrating hardware and/or software components of an exemplary mobile device according to some embodiments of the present disclosure.

FIG. 3 is a schematic diagram illustrating exemplary hardware components and/or software components of an exemplary mobile device according to some embodiments of the present disclosure. In some embodiments, one or more components (e.g., the terminal device 130 and/or the processing device 140) of the image processing system 100 may be implemented on the mobile device 300.

As illustrated in FIG. 3, the mobile device 300 may include a display 310, a communication platform 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the image processing system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4A:
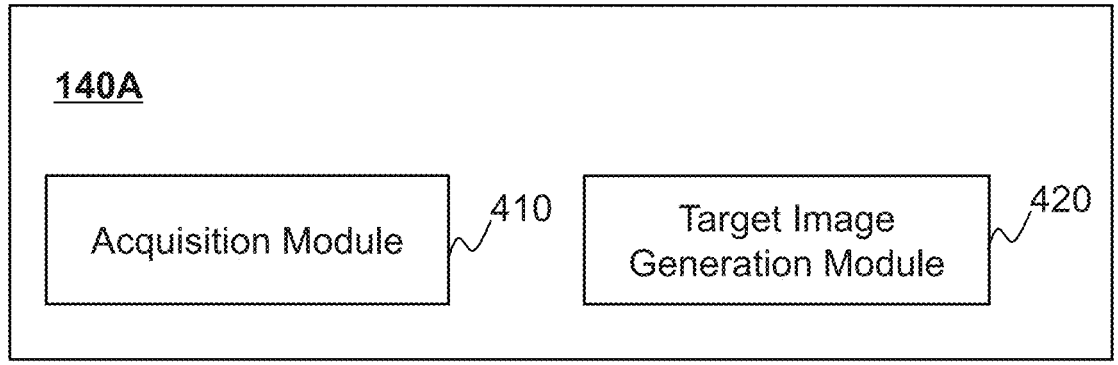
FIG. 4A is a block diagram illustrating an exemplary processing device according to some embodiments of the present disclosure.
Figure 4B:
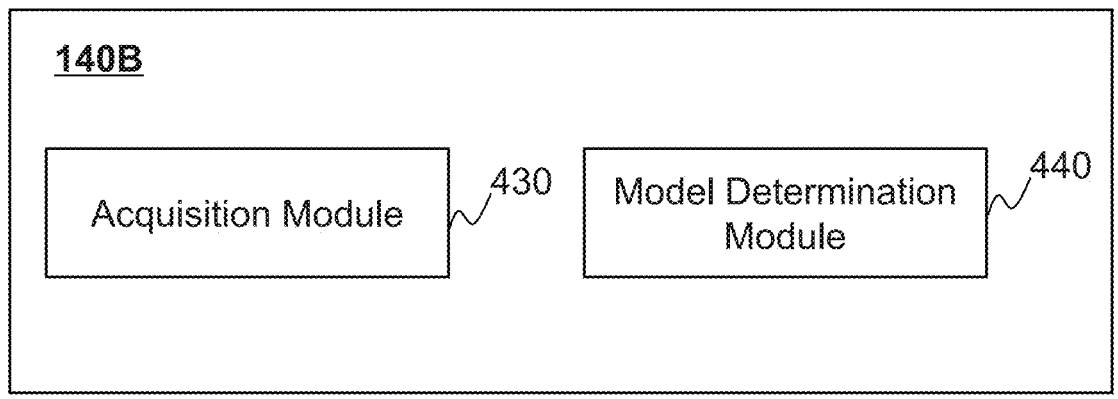
FIG. 4B is a block diagram illustrating an exemplary processing device according to some embodiments of the present disclosure.

FIGS. 4A and 4B are block diagrams illustrating exemplary processing devices according to some embodiments of the present disclosure. The processing devices 140A and 140B may be exemplary processing devices 140 as described in connection with FIG. 1. In some embodiments, the processing device 140A may be configured to apply a trained image processing model in reconstructing a target image of a subject. The processing device 140B may be configured to generate a trained image processing model by model training. In some embodiments, the processing devices 140A and 140B may be respectively implemented on a processing unit (e.g., the processor 210 illustrated in FIG. 2 or the CPU 340 illustrated in FIG. 3). Merely by way of example, the processing devices 140A may be implemented on a CPU 340 of a terminal device, and the processing device 140B may be implemented on a computing device 200. Alternatively, the processing devices 140A and 140B may be implemented on a same computing device 200 or a same CPU 340. For example, the processing devices 140A and 140B may be implemented on a same computing device 200.

As illustrated in FIG. 4A, the processing device 140A may include an acquisition module 410 and a target image generation module 420.

The acquisition module 410 may be configured to obtain an initial image of a subject acquired by an imaging device according to a tracer. In some embodiments, the imaging device may include a PET device, a SPECT device, a PET-MRI device, a PET-CT device, a SPECT-CT device, etc. The tracer may not be commonly used.

The target image generation module 420 may be configured to generate a target image based on the initial image using a trained image processing model corresponding to the tracer. The target image may have a higher image quality than the initial image. The target image generation module 420 may input the initial image into the trained image processing model to determine the target image.

As illustrated in FIG. 4B, the processing device 140B may include an acquisition module 430 and a model determination module 440.

The acquisition module 430 may be configured to obtain training samples. The training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image. In some embodiments, the acquisition module 430 may reconstruct the reference first image based on first imaging data using a first PET image reconstruction technique. The acquisition module 430 may further generate the corresponding sample first image by down-sampling the first imaging data. Similarly, the acquisition module 430 may reconstruct the reference second image based on the second imaging data using a second PET image reconstruction technique. The acquisition module 430 may further generate the corresponding sample second image by down-sampling the second imaging data. In such cases, the reference second image may have a higher image quality than the corresponding sample second image.

The model determination module 440 may be configured to generate a trained image processing model by training a preliminary model using the training samples in a training process. The training process may include a plurality of iterations.

In some embodiments, during an iteration of the plurality of iterations, the model determination module 440 may input the at least one sample first image and the at least one sample second image into a first intermediate model randomly or in a preset order. The first intermediate model may output at least one first prediction output corresponding to the at least one sample first image and at least one second prediction output corresponding to the at least one sample second image. The first intermediate model may be the preliminary model in the first iteration of the plurality of iterations, or an updated model generated in a previous iteration. The model determination module 440 may determine whether a termination condition is satisfied. In response to a determination that the termination condition is satisfied, the model determination module 440 may designate the first intermediate model as the trained image processing model.

In some embodiments, the training process may include a first training process and a second training process. During the first training process, the model determination module 440 may generate a second intermediate model by training the preliminary model using the at least one sample first image and the at least one reference first image of the training samples. During the second training process, the model determination module 440 may generate the trained image processing model by training the second intermediate model using the at least one sample second image and the at least one reference second image of the training samples.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 140A and/or the processing device 140B may share two or more of the modules, and any one of the modules may be divided into two or more units. For instance, the processing devices 140A and 140B may share a same acquisition module; that is, the acquisition module 410 and the acquisition module 430 are a same module. In some embodiments, the processing device 140A and/or the processing device 140B may include one or more additional modules, such as a storage module (not shown) for storing data. In some embodiments, the processing device 140A and the processing device 1406 may be integrated into one processing device 140.

Figure 5:
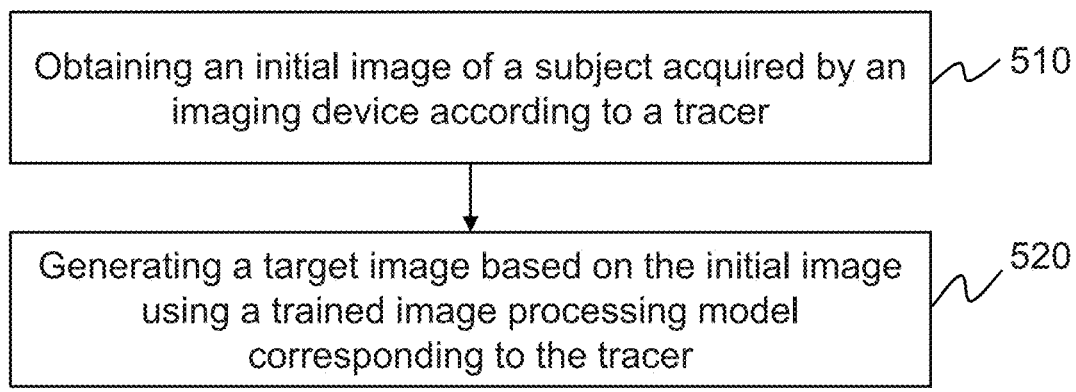
FIG. 5 is a flowchart illustrating an exemplary process for generating a trained image processing model according to some embodiments of the present disclosure.

FIG. 5 is a flowchart illustrating an exemplary process for generating a target image according to some embodiments of the present disclosure. In some embodiments, a process 500 may be implemented as a set of instructions (e.g., an application) stored in the storage device 150, the storage 220, or the storage 390. The processing device 140A (e.g., implemented on the processing device 140, the processor 210, the CPU 340, and/or one or more modules illustrated in FIG. 4A) may execute the set of instructions, and when executing the instructions, the processing device 140A may be configured to perform the process 500. The operations of the illustrated process 500 presented below are intended to be illustrative. In some embodiments, the process 500 may be accomplished with one or more additional operations not described, and/or without one or more of the operations discussed. Additionally, the order of the operations of the process 500 illustrated in FIG. 5 and described below is not intended to be limiting.

In 510, the processing device 140A (e.g., the acquisition module 410) may obtain an initial image of a subject acquired by an imaging device according to a tracer.

The subject may be biological or non-biological. For example, the subject may include a patient, a man-made object, etc. as described elsewhere in the present disclosure (e.g., FIG. 1 and the descriptions thereof). In some embodiments, the initial image may be obtained from the imaging device (e.g., the imaging device 110), the storage device 150, or any other storage device. For example, the imaging device may transmit acquired imaging data (e.g., projection data) to the storage device 150 or any other storage device for storage. The processing device 140A may retrieve the imaging data from the storage device 150 or any other storage device and generate the initial image based on the retrieved imaging data. As another example, the processing device 140A may obtain the initial image from the imaging device directly.

In some embodiments, the imaging device may include a PET device, a SPECT device, a PET-MRI device, a PET-CT device, a SPECT-CT device, etc., as described elsewhere in the present disclosure (e.g., FIG. 1 and the descriptions thereof). The initial image may be generated based on the imaging data (e.g., projection data) acquired by the imaging device (e.g., a PET device) after the tracer (or radioactive tracer) is injected into the subject. In some embodiments, the imaging data used to generate the initial image may be obtained by down-sampling to save scanning time. In some embodiments, the tracer may include $^{18}$F-FDG, $^{68}$Ga-PSMA, Yttrium-90 labeled substances (Yttrium-90), $^{18}$F-labeled dopamine ($^{18}$F-FDOPA), or the like, or any combination thereof. In some embodiments, the tracer may be a tracer that is not commonly used, e.g., a tracer that is difficult to prepare, a novel tracer, or a tracer that is expensive.

In 520, the processing device 140A (e.g., the target image generation module 420) may generate a target image based on the initial image using a trained image processing model corresponding to the tracer. The target image may have a higher image quality than the initial image.

The trained image processing model may be configured to generate an image of a specific subject with relatively high image quality based on a specific image of the specific subject with relatively low image quality. In other words, the processing device 140A may optimize the initial image to generate the target image using the trained image processing model. In some embodiments, an image quality of an image may be measured by one or more image parameters. Exemplary image parameters of an image may include a signal-to-noise ratio (SNR), an image resolution, a contrast, a brightness, or the like, or any combination thereof. An optimized image (i.e., the target image) may have a lower noise, a higher contrast, a higher brightness, a higher resolution, etc., than the initial image.

In some embodiments, the trained image processing model may be constructed based on a U-Net model, a Res-Net model, a V-Net model, a U-Net++ model, a Feedback-Net model, or the like, or any combination thereof.

Different tracers may correspond to different trained image processing models. As used herein, the trained image processing model corresponding to the tracer may refer to a model that is trained using training samples including at least some sample images generated based on the tracer. For example, the training samples may include a plurality of sample first images generated based on a first tracer, a plurality of reference first images each of which corresponds to one of the plurality of sample first images and has a higher image quality than the corresponding sample first image, a plurality of sample second images generated based on a second tracer different from the first tracer, and a plurality of reference second images each of which corresponds to one of the plurality of sample second images and has a higher image quality than the corresponding sample second image. The second tracer may be the tracer corresponding to the initial image.

In some embodiments, the processing device 140A may retrieve the trained image processing model from the storage device 150, the terminal device 130, or any other storage device. For example, the trained image processing model may be obtained by training a preliminary model offline using a processing device (e.g., the processing device 140B) (e.g., an external device of the image processing system 100) different from or same as the processing device 140A. The processing device may store the trained image processing model in the storage device 150, the terminal device 130, or any other storage device. The processing device 140A may retrieve the trained image processing model from the storage device 150, the terminal device 130, or any other storage device in response to receipt of a request for image processing. More descriptions regarding the training of the preliminary model may be found elsewhere in the present disclosure (e.g., FIGS. 6-8 and the descriptions thereof).

The processing device 140A may input the initial image into the trained image processing model to determine the target image. In some embodiments, the processing device 140A may transmit the target image to a terminal device (e.g., the terminal device 130) for display.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, one or more operations may be omitted and/or one or more additional operations may be added. For example, one or more other optional operations (e.g., a preprocessing operation, a model obtaining operation, etc.) may be added before operation 520. In some embodiments, the preprocessing operation on the imaging data may include a denosing operation, an enhancement operation, a filtering operation, or the like, or any combination thereof.

FIG. 6 is a flowchart illustrating an exemplary process for generating a trained image processing model according to some embodiments of the present disclosure. In some embodiments, a process 600 may be implemented as a set of instructions (e.g., an application) stored in the storage device 150, the storage 220, or the storage 390. The processing device 140B (e.g., implemented on the processing device 140, the processor 210, the CPU 340, one or more modules illustrated in FIG. 4B, or an external device of the image processing device 100) may execute the set of instructions, and when executing the instructions, the processing device 140B may be configured to perform the process 600. The operations of the illustrated process 600 presented below are intended to be illustrative. In some embodiments, the process 600 may be accomplished with one or more additional operations not described, and/or without one or more of the operations discussed. Additionally, the order of the operations of the process 600 illustrated in FIG. 6 and described below is not intended to be limiting. In some embodiments, the trained image processing model described in connection with operation 520 in FIG. 5 may be obtained according to the process 600. In some embodiments, the process 600 may be performed by another device or system other than the image processing system 100, e.g., a device or system of a vendor of a manufacturer. For illustration purposes, the implementation of the process 600 by the processing device 140B is described as an example.

In 610, the processing device 140B (e.g., the acquisition module 430) may obtain training samples.

In some embodiments, at least a portion of the training samples may be retrieved from a storage device (e.g., the storage device 150) disclosed elsewhere in the present disclosure. For example, the storage device may include a database, multiple training samples may be previously generated and stored in the database. The processing device 140B may retrieve the multiple training samples from the database. In some embodiments, at least a portion of the training samples may be generated by the processing device 140B. For example, during a medical scanning process of the imaging device 110, a subject may be placed on the scanning table 114 and scanned in the detection region 113 by the imaging device 110. The detector assembly 112 may detect radiation (e.g., gamma photons) and generate electrical signals. The electronic module 115 may process the electrical signals and generate imaging data. Further, the processing device 140B may obtain the imaging data from the electronic module 115 and process the imaging data to generate a training sample.

The training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image. In some embodiments, a sample first image and the corresponding reference first image, or a sample second image and the corresponding reference second image may form a training sample set. In other words, the training samples may include at least one first training sample set and at least one second training sample set.

In some embodiments, the tracers (e.g., the first tracer or the second tracer) may include $^{18}$F-FDG, $^{68}$Ga-PSMA, Yttrium-90, $^{18}$F-FDOPA, etc. In some embodiments, the first tracer may be a tracer commonly used in imaging scans of an imaging device (e.g., a PET device). The second tracer may be a tracer that is rarely used in the imaging scans of the imaging device. For example, the second tracer may be more difficult to prepare than the first tracer. As another example, the first tracer may be cheaper than the second tracer. For illustration purposes, $^{18}$F-FDG may be taken as an exemplary first tracer, and $^{68}$Ga-PSMA may be taken as an exemplary second tracer in the present disclosure.

As a glucose analogue, $^{18}$F-FDG can be taken up by cells with high utilization of glucose such as the brain, a kidney, cancer cells, etc. In such cells with high utilization of glucose, a phosphorylation process may prevent the release of glucose from the cells in its original form. Since the 2-position oxygen in glucose is necessary for subsequent glycolysis, $^{18}$F-FDG may be the same as 2-deoxy-D-glucose and may not continue to be metabolized in the cells. In this way, before the radioactive decay, the produced $^{18}$F-FDG-6-phosphate may not undergo glycolysis. As a result, the distribution of $^{18}$F-FDG may reflect the distribution of glucose uptake and phosphorylation in cells in vivo. In some embodiments, $^{18}$F-FDG may be used to assess the glucose metabolism of the heart, lungs, the train, etc. In some embodiments, $^{18}$F-FDG may be used for tumor imaging in oncology. After being taken up by the cell, $^{18}$F-FDG may be phosphorylated by hexokinase (in fast-growing malignant tumors, the hexokinase in mitochondria is significantly increased) and retained by metabolically active tissues, such as most types of malignant tumors. Therefore, $^{18}$F-FDG may be used for the diagnosis, staging, and treatment monitoring of cancer, especially for Hodgkin's disease, non-Hodgkin's lymphoma, colorectal cancer, breast cancer, melanoma, and lung cancer. Moreover, $^{18}$F-FDG has been used for the diagnosis of Alzheimer's disease.

PSMA is a membrane protein that expresses at a low level in normal tissues (except kidneys) but is highly up-regulated in prostate cancer cells. A radiolabeled PSMA tracer, such as $^{68}$Ga-PSMA, may be used for the diagnosis and localization of prostate cancer through an imaging device, such as a PET/CT device. $^{68}$Ga-PSMA may have normal physiological distribution in organs, such as salivary glands, the liver, the spleen, a kidney, the small intestine, the bladder, etc. In other words, the high concentration of radionuclides found in the above-mentioned organs does not necessarily represent the spread of tumors. At present, one of the important driving forces to promote the research and development of $^{68}$Ga-labeled tracer may be the need to make up for the defects of $^{18}$F-FDG in the diagnosis of some diseases. For example, prostate cancer is one of the "blind spot" in using $^{18}$F-FDG for cancer diagnosis. More than half of the prostate cancers and their metastases diagnosed using radionuclides labeled FDG (e.g., $^{18}$F-FDG) reported in prior arts are false-negatives, and due to the non-specificity of $^{18}$F-FDG in distinguishing tumors and inflammations, about 20% of prostate with increased $^{18}$F-FDG uptake is confirmed to be prostate cancer. However, although a relatively ideal technology for labeling PSMA with $^{68}$Ga has been discovered, the training data for training an image processing model corresponding to $^{68}$Ga-PSMA is still scarce due to the difficulty of preparing $^{68}$Ga-PSMA.

In some embodiments, for a first training sample set, a reference first image may be generated based on first imaging data acquired by an imaging device after a first sample subject is injected with the first tracer. Specifically, the imaging device may scan the first sample subject to generate the first imaging data after the first tracer is injected into the first sample subject. The processing device 140B may reconstruct the reference first image based on the first imaging data using a first PET image reconstruction technique. Exemplary PET image reconstruction techniques may include an iterative reconstruction algorithm, a Fourier slice theorem algorithm, a filtered back projection (FBP) algorithm, a fan-beam reconstruction algorithm, an analytic reconstruction algorithm, or the like, or any combination thereof. The processing device 140B may further generate the corresponding sample first image by down-sampling the first imaging data. In such cases, the reference first image may have a higher image quality (e.g., measured by one or more image parameters as described in connection with FIG. 5) than the corresponding sample first image. Similarly, for a second training sample set, a reference second image may be generated based on second imaging data acquired by the imaging device after a second sample subject is injected with the second tracer. Specifically, the imaging device may scan the second sample subject to generate the second imaging data after the second tracer is injected into the second sample subject. The processing device 140B may reconstruct the reference second image based on the second imaging data using a second PET image reconstruction technique. The processing device 140B may further generate the corresponding sample second image by down-sampling the second imaging data. In such cases, the reference second image may have a higher image quality than the corresponding sample second image. In some embodiments, the first PET image reconstruction technique may be the same as or different from the second PET image reconstruction technique.

In some embodiments, the first sample subject may be the same as or different from the second sample subject. In some embodiments, the second sample subject of a training sample set may be of the same type as or a different type from the subject as described in connection with operation 510 in FIG. 5. As used herein, two subjects are deemed to be of a same type when they belong to a same type of organ or tissue. For example, the subject may be the head of a patient, and the second sample subject may be the head of another patient or a phantom of a human head.

In some embodiments, in the training samples, a first count of the sample first images or the reference first images may be greater than a second count of the sample second images or the reference second images.

In 620, the processing device 140B (e.g., the model determination module 440) may generate a trained image processing model by training a preliminary model using the training samples in a training process.

In some embodiments, the preliminary model may include a deep neural network (DNN) model, a convolutional neural network (CNN) model, a recurrent neural network (RNN) model, a feature pyramid network (FPN) model, etc. Exemplary CNN models may include a U-Net model, a Res-Net model, a V-Net model, a U-Net++ model, a Feedback-Net (FB-Net) model, or the like, or any combination thereof. An exemplary FB-Net model may be a Feedback Convolutional Neural Network (FB-CNN) including a plurality of sequentially connected subnets. More descriptions regarding the FB-CNN may be found elsewhere in the present disclosure. See, e.g., FIG. 9, FIG. 10, and the descriptions thereof.

In some embodiments, the preliminary model may include a plurality of parameters, such as architecture parameters, learning parameters, etc. The plurality of parameters may also be referred to as training parameters. One or more parameter values of the plurality of parameters (e.g., the learning parameters) may be altered during the training of the preliminary model using the training samples. The parameter values of the plurality of parameters may be initialized, set, and/or adjusted before the training of the preliminary model to obtain an initialized preliminary model. Exemplary parameters of the preliminary model may include the size of a kernel of a layer, the total count (or number) of layers, the count (or number) of nodes in each layer, a learning rate, a batch size, an epoch, a connected weight between two connected nodes, a bias vector relating to a node, etc.

The preliminary model may be trained based on the training samples using a training algorithm. Exemplary training algorithms may include a gradient descent algorithm, Newton's algorithm, a Quasi-Newton algorithm, a Levenberg-Marquardt algorithm, a conjugate gradient algorithm, or the like, or any combination thereof. In some embodiments, the trained image processing model may be obtained by performing a plurality of iterations to iteratively update one or more parameter values of the preliminary model (or an intermediate model). Before the plurality of iterations, the parameter values of the preliminary model may be initialized. For example, the connected weights and/or the bias vector of nodes of the preliminary model may be initialized to be random values in a range, e.g., the range from −1 to 1. As another example, all the connected weights of the preliminary model may have the same value in the range from −1 to 1, for example, 0. As still an example, the bias vector of nodes in the preliminary model may be initialized to be random values in a range from 0 to 1. In some embodiments, the parameter values of the preliminary model may be initialized based on a Gaussian random algorithm, a Xavier algorithm, etc.

In some embodiments, the training process may include a plurality of iterations. The at least one sample first image and the at least one sample second image in the training samples may serve as inputs of the training process. The at least one reference first image and the at least one reference second image in the training samples may serve as reference outputs of the training process. During the training process, first prediction outputs corresponding to the sample first images and second prediction outputs corresponding to the sample second images may be determined. The processing device 140B may generate the trained image processing device based on first differences between the first prediction outputs and the corresponding reference first images and second differences between the second prediction outputs and the corresponding reference second images.

In some embodiments, during an iteration of the plurality of iterations, the processing device 140B may input the at least one sample first image and the at least one sample second image into a first intermediate model randomly or in a preset order. The first intermediate model may output at least one first prediction output corresponding to the at least one sample first image and at least one second prediction output corresponding to the at least one sample second image. The first intermediate model may be the preliminary model in the first iteration of the plurality of iterations, or an updated model generated in a previous iteration. The processing device 140B may determine whether a termination condition is satisfied. The termination condition may provide an indication of whether the preliminary model is sufficiently trained. In response to a determination that the termination condition is satisfied, the processing device 140B may designate the first intermediate model as the trained image processing model. On the other hand, in response to a determination that the termination condition is not satisfied, the processing device 140B may update the parameter values of the first intermediate model until the termination condition is satisfied.

In some embodiments, the termination condition may relate to a loss function or an iteration count of the plurality of iterations (or training process). For example, the termination condition may be satisfied if the value of the loss function associated with the preliminary model is minimal or smaller than a threshold (e.g., a constant). As another example, the termination condition may be satisfied if the value of the loss function converges. The convergence may be deemed to have occurred if the variation of the values of the loss function in two or more consecutive iterations is smaller than a threshold (e.g., a constant). As still an example, the termination condition may be satisfied when a specified number (or count) of iterations are performed in the training process.

In some embodiments, the processing device 140B may obtain a first preliminary weight for each of the at least one sample first image and a second preliminary weight for each of the at least one sample second image. The processing device 140B may determine the loss function based on the first preliminary weights and the second preliminary weights. The processing device 140B may generate the trained image processing model by training the preliminary model based on the loss function. More descriptions regarding the training of the preliminary model associated with weights may be found elsewhere in the present disclosure. See, e.g., FIG. 7 and the descriptions thereof.

In some embodiments, the training process may include a first training process and a second training process. During the first training process, the processing device 140B may generate a second intermediate model by training the preliminary model using the at least one sample first image and the at least one reference first image of the training samples. During the second training process, the processing device 140B may generate the trained image processing model by training the second intermediate model using the at least one sample second image and the at least one reference second image of the training samples. More descriptions regarding the training of the second intermediate model including a first training process and a second training process may be found elsewhere in the present disclosure. See, e.g., FIG. 8 and the descriptions thereof.

In some embodiments, if the first count of the at least one sample first image or the at least one reference first image in the training samples is greater than the second count of the at least one sample second image or the at least one reference second image in the training samples, the trained image processing model trained using the training samples may correspond to the second tracer. That is, the trained image processing model may be used to process images generated based on the second tracer. By using the training samples, due to the participation of a large amount of first training sample sets (including training samples corresponding to the first tracer), the preliminary model may be trained with enough training samples. Further, a small amount of the second training sample sets (including training samples corresponding to the second tracer) may also participate the training process. Therefore, even if the training data of the second tracer is few, an image processing model can be trained and tuned correspond to the second tracer.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140B may generate the trained image processing model by training the preliminary model using the training samples and additional training sample sets, e.g., a plurality of sample third images generated based on a third tracer and a plurality of reference third images each of which corresponds to one of the plurality of sample third images and has a higher image quality than the corresponding sample third image. In some embodiments, one or more operations may be added or omitted. For example, after the trained image processing model is generated, the processing device 140B may further test the trained image processing model using a set of testing samples. Additionally or alternatively, the processing device 140B may update the trained image processing model periodically or irregularly based on one or more newly-generated training samples.

Figure 7:
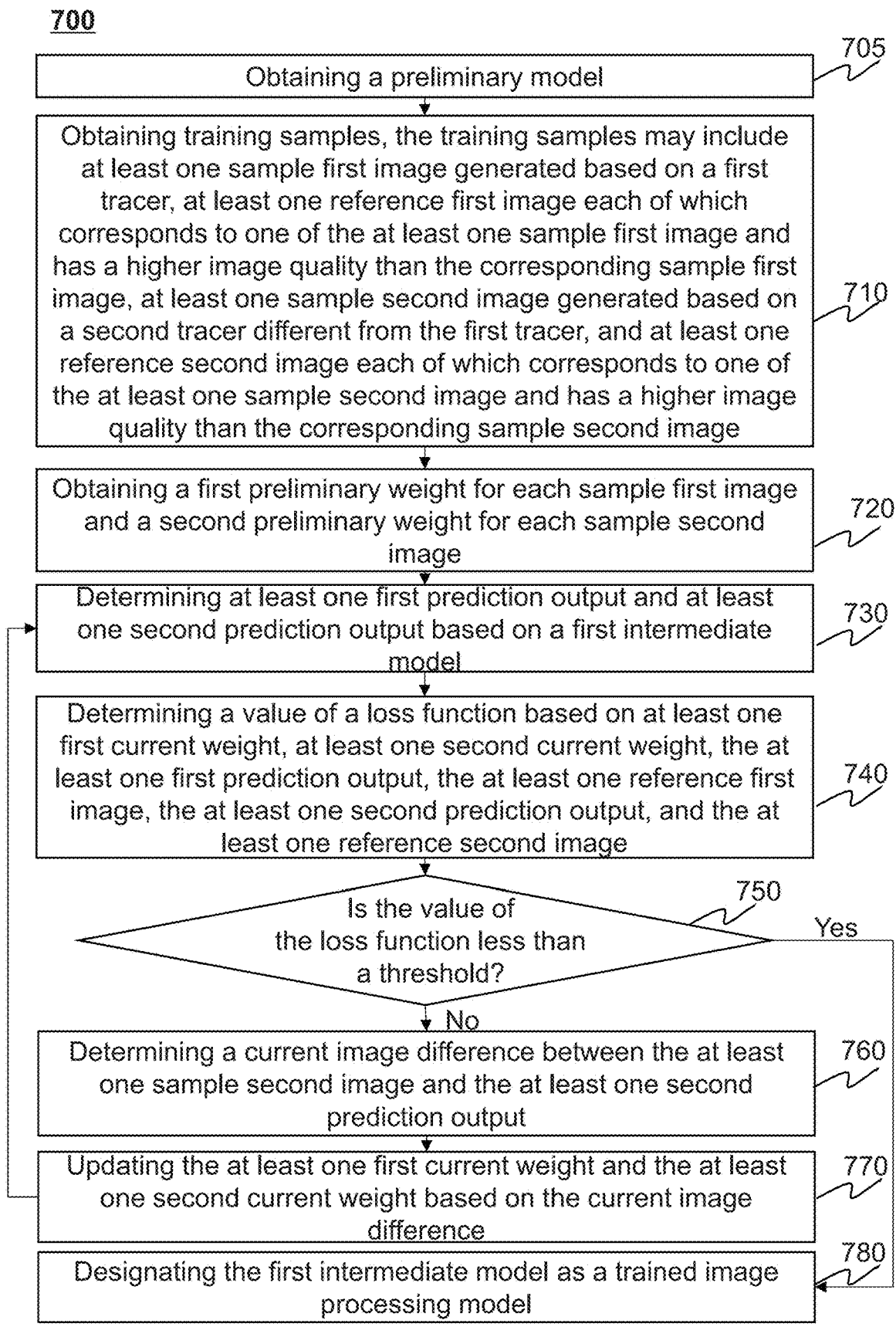
FIG. 7 is a flowchart illustrating an exemplary process for generating a trained image processing model according to some embodiments of the present disclosure.

FIG. 7 is a flowchart illustrating an exemplary process for generating a trained image processing model according to some embodiments of the present disclosure. In some embodiments, a process 700 may be implemented as a set of instructions (e.g., an application) stored in the storage device 150, the storage 220, or the storage 390. The processing device 140B (e.g., implemented on the processing device 140, the processor 210, the CPU 340, one or more modules illustrated in FIG. 4B, or an external device of the image processing device 100) may execute the set of instructions, and when executing the instructions, the processing device 140B may be configured to perform the process 700. The operations of the illustrated process 700 presented below are intended to be illustrative. In some embodiments, the process 700 may be accomplished with one or more additional operations not described, and/or without one or more of the operations discussed. Additionally, the order of the operations of the process 700 illustrated in FIG. 7 and described below is not intended to be limiting. In some embodiments, one or more operations of the process 700 may be performed to achieve at least part of operation 620 as described in connection with FIG. 6. In some embodiments, the process 700 may be performed by another device or system other than the image processing system 100, e.g., a device or system of a vendor of a manufacturer.

In 705, the processing device 140B (e.g., the acquisition module 430) may obtain a preliminary model.

In some embodiments, the preliminary model may include a DNN model, a CNN model (e.g., e.g., a U-Net model, or an FB-CNN model), a recurrent neural network (RNN) model, a feature pyramid network (FPN) model, or the like, or any combination thereof. In some embodiments, the preliminary model may be stored in one or more storage devices (e.g., the storage device 150, the storage 220, and/or the storage 390) associated with the image processing system 100 and/or an external data source. Accordingly, the preliminary model may be retrieved from the storage devices and/or the external data source.

In some embodiments, the processing device 140B may perform a plurality of iterations to iteratively update one or more parameter values of the preliminary model. Before the plurality of iterations, the processing device 140B may initialize the parameter values of the preliminary model. In some embodiments, the one or more parameters may be set randomly. In some embodiments, the one or more parameters may be set to one or more certain values, e.g., 0, 1, or the like. In some embodiments, the parameter values of the preliminary model may be initialized based on a Gaussian random algorithm, a Xavier algorithm, etc.

In 710, the processing device 140B (e.g., the acquisition module 430) may obtain training samples. The training samples may include at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image.

For one of the at least one training sample, the processing device 140B may determine a reference first image generated based on first imaging data acquired by an imaging device (e.g., a PET device) according to the first tracer (e.g., $^{18}$F-FDG). The processing device 140 may generate the corresponding sample first image by down-sampling the first imaging data. In such cases, the reference first image may have a higher image quality (e.g., measured by one or more image parameters as described in connection with FIG. 5) than the corresponding sample first image. Similarly, the processing device 140B may determine a reference second image generated based on second imaging data acquired by the imaging device according to the second tracer (e.g., $^{68}$Ga-PSMA). The processing device 140 may generate the corresponding sample second image by down-sampling the second imaging data. In such cases, the reference second image may have a higher image quality than the corresponding sample second image.

In some embodiments, a first count N (N≥1) of the at least one first training sample set (i.e., the at least one sample first image and the at least one reference first image) may be greater than a second count M of the at least one second training sample set (i.e., the at least one sample second image and the at least one reference second image), wherein N and M are both positive integers, and 1≤M≤N.

In 720, the processing device 140B (e.g., the model determination module 440) may obtain a first preliminary weight for each sample first image and a second preliminary weight for each sample second image. In some embodiments, the processing device 140B may update the first preliminary weight for each sample first image and the second preliminary weight for each sample second image.

In some embodiments, the second preliminary weight may be greater than the first preliminary weight. In some embodiments, the first preliminary weight may be associated with the first count N of the at least one first training sample set. The second preliminary weight may be associated with the second count M of the at least one second training sample set.

Merely by way of example, each training sample set in the training samples may correspond to a label number i. Specifically, for the first training sample sets, the label number i of each first training sample set (or each sample first image) may belong to [1, N], i.e., i∈[1, N]. For the second training sample sets, the label number i of each second training sample set (or each sample second image) may belong to [N+1, N+M], i.e., i∈[N+1, N+M]. The first preliminary weights and the second preliminary weights may be determined according to Equation (1) as follows:

$$w_i^0 = \begin{cases} 1/N & i = 1, \ldots, N \\ 1/M & i = N+1, \ldots, N+M \end{cases}, \quad (1)$$

where $w_i^0$ denotes the first preliminary weight of a sample first image with the i-th label number (also be referred to as the i-th sample first image for brevity) or the second preliminary weight of a sample second image with the i-th label number (also be referred to as the i-th sample second image for brevity).

In 730, the processing device 140B (e.g., the model determination module 440) may determine at least one first prediction output and at least one second prediction output based on a first intermediate model. The first intermediate model may be the preliminary model in the first iteration of the plurality of iterations, or an updated model generated in a previous iteration.

The processing device 140B may input the at least one sample first image into the first intermediate model, and the first intermediate model may output the at least one first prediction output. Similarly, the processing device 140B may input the at least one sample second image into the first intermediate model, and the first intermediate model may output the at least one second prediction output.

In 740, the processing device 140B (e.g., the model determination module 440) may determine a value of a loss function based on at least one first current weight, at least one second current weight, the at least one first prediction output, the at least one reference first image, the at least one second prediction output, and the at least one reference second image. The first current weight may be the first preliminary weight in the first iteration of the plurality of iterations, or an updated value related to the first preliminary weight generated in the previous iteration. The second current weight may be the second preliminary weight in the first iteration of the plurality of iterations, or an updated value related to the second preliminary weight generated in the previous iteration.

In some embodiments, the processing device 140B may perform a normalization operation on the at least one first current weight and the at least one second current weight. Merely by way of example, the normalization operation may be performed according to Equation (2) as follows:

$$p_i^t = \frac{w_i^t}{\sum_{i=1}^{N+M} w_i^t}, \quad (2)$$

where t denotes the t-th iteration, wherein t=0, 1, 2, . . . , T; $p_i^t$ denotes the normalized weight of the i-th sample first image in the t-th iteration; and $w_i^t$ denotes the current first weight of the i-th sample first image in the t-th iteration or the second current weight of the i-th sample second image in the t-th iteration.

In some embodiments, the loss function may include a first term at least related to the at least one first current weight and a second term at least related to the at least one second current weight. Merely by way of example, the processing device 140B may determine the value of the loss function according to Equation (3) as follows:

$$L^t = \sum_1^N p_i^t |RH_i^F - H_i^F| + \sum_{N+1}^M p_i^t |RH_i^G - H_i^G|, \quad (3)$$

where L denotes the loss function; $H_i^F$ denotes the i-th reference first image; $H_i^G$ denotes the i-th reference second image; $RH_i^F$ denotes the i-th first prediction output corresponding to the i-th sample first image, wherein $RH_i^F = NN^t(L_i^F)$, and $L_i^F$, denotes the i-th sample first image; $RH_i^G$ denotes the i-th second prediction output corresponding to the i-th sample second image, wherein $RH_i^G = NN^t(L_i^G)$, and $L_i^G$ denotes the i-th sample second image.

In 750, the processing device 140B (e.g., the model determination module 440) may determine whether the value of the loss function is less than a loss threshold. The loss threshold may be set according to a default setting of the image processing system 100 or preset by a user or operator via the terminal device 130.

In response to a determination that the value of the loss function is less than the loss threshold, the processing device 140B may designate the first intermediate model as the trained image processing model in operation 780. On the other hand, in response to a determination that the value of the loss function is greater than the loss threshold, the processing device 140B may update at least one parameter of the first intermediate model based on the value of the loss function and further proceed to perform operation 760.

In 760, the processing device 140B (e.g., the model determination module 440) may determine a current image difference between the at least one reference second image and the at least one second prediction output. In some embodiments, the processing device 140B may determine pixel differences between a plurality of pixels of the at least one reference second image and a plurality of pixels of the at least one second prediction output. The processing device 140B may determine the current image difference based on the pixel differences and the second current weights.

Merely by way of example, the processing device 140B may determine the current image difference according to Equation (4) as follows:

$$\eta^t = \frac{\sum_{N+1}^M w_i^t |RH_i^G - H_i^G|}{\sum_{N+1}^M w_i^t}, \quad (4)$$

where $\eta^t$ denotes the image difference of the t-th iteration (i.e., the current image difference).

In some embodiments, the processing device 140B may determine that a termination condition is satisfied if a value of the current image difference is smaller than a threshold (e.g., a constant). The processing device 140B may designate the currently updated first intermediate model as the trained image processing model.

In 770, the processing device 140B (e.g., the model determination module 440) may update the at least one first current weight and the at least one second current weight based on the current image difference.

In some embodiments, the processing device 140B may obtain an initial factor. The processing device 140B may determine a target factor by comparing the current image difference of the current iteration and a previous image difference that corresponds to the current image difference and is determined in the previous iteration. The processing device 140B may update the at least one first current weight and the at least one second current weight based on the comparison. For example, in response to determining that the current image difference is greater than the previous image difference, the processing device 140B may decrease the at least one first current weight and increase the at least one second current weight. On the contrary, in response to determining that the current image difference is less than the previous image difference, the processing device 140B may increase the at least one first current weight and decrease the at least one second current weight.

Merely by way of example, the target factor may be determined according to Equation (5) as follows:

$$\beta_t = \begin{cases} \beta_0 & \eta^t \geq \eta^{t-1} \\ \frac{1}{\beta_0} & \eta^t < \eta^{t-1} \end{cases}, \quad (5)$$

where $\beta_0$ denotes the initial factor, and $\beta_0 < 1$; $\beta_t$ denotes the target factor; $\eta^{t-1}$ denotes an image difference of the (t−1)-th iteration (i.e., the previous image difference).

The processing device 140B may adjust the at least one first current weight and the at least one second current weight according to Equation (6) as follows:

$$w_i^{t+1} = \begin{cases} w_i^t \beta_t & i = 1, \ldots, N \\ w_i^t / \beta_t & i = N+1, \ldots, N+M \end{cases}, \quad (6)$$

where $w_i^{t+1}$ denotes the first current weight of the i-th sample first image in the (t+1)-th iteration (i.e., the next iteration) or the second current weight of the i-th sample second image in the (t+1)-th iteration.

In some embodiments, the processing device 140B may generate another current image different between the at least one sample first image and the at least one first prediction output. The processing device 140B may update the at least one first current weight and the at least one second current weight based on the current image difference corresponding to the second tracer and/or the current image difference corresponding to the first tracer.

After adjusting the at least one first current weight and the at least one second current weight, the processing device 140B may execute the process 700 to return operation 730 to update the at least one first prediction output and the at least one second prediction output based on an updated first intermediate model.

According to the process 700, the trained image processing model is trained using sample data corresponding to the first tracer and the second tracer. If the second tracer is not commonly used (i.e., training data corresponding to the second tracer is few), the trained image processing model corresponding to the second tracer may still be generated due to the participation of a large amount of sample data corresponding to the first tracer in the training process, that is, the trained image processing model trained using sample data corresponding to the first tracer and the second tracer can be used to process images generated based on the second tracer.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140B may update the trained image processing model at a certain time interval (e.g., per month, per two months) based on a plurality of newly obtained scanning records.

Figure 8:
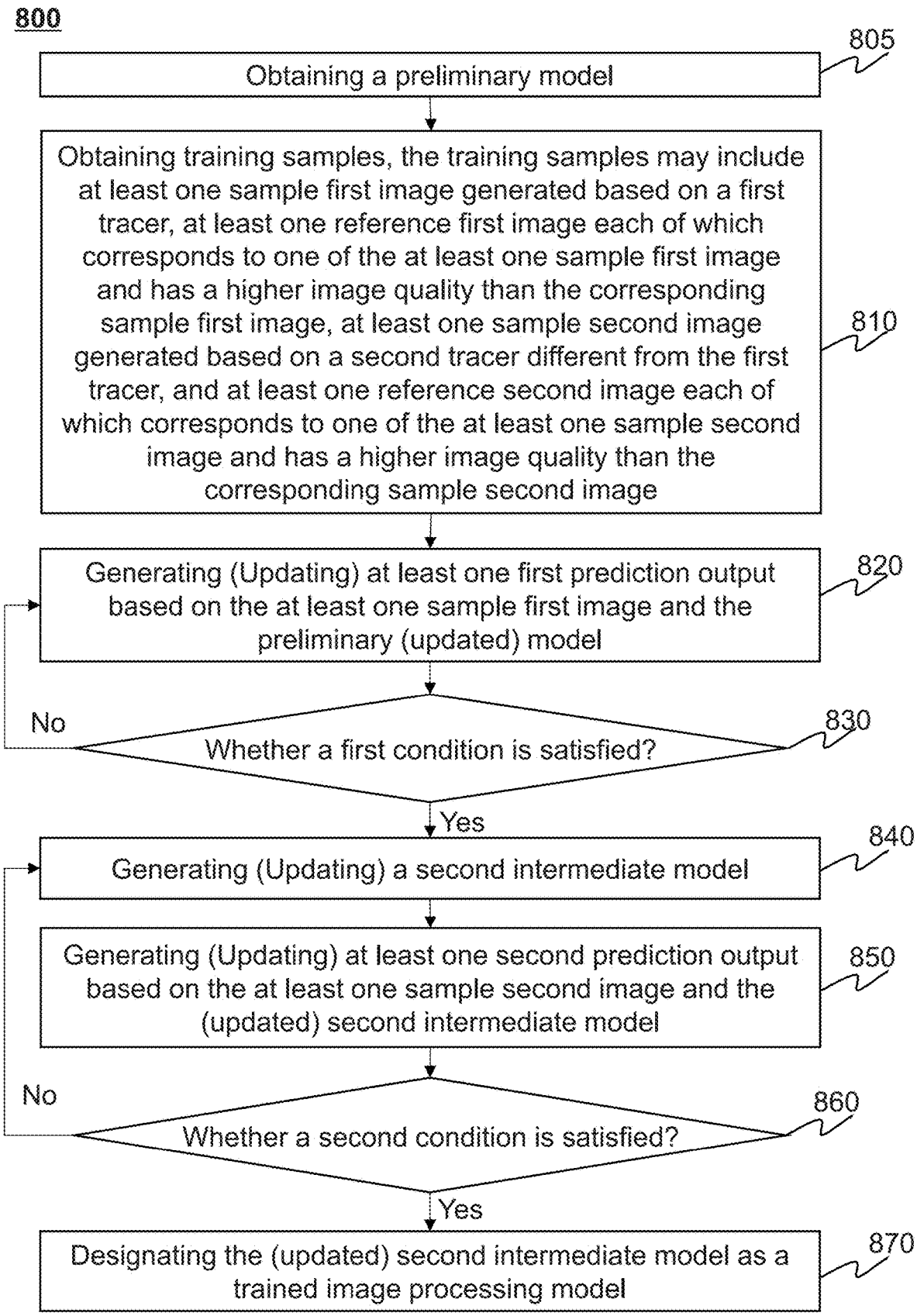
FIG. 8 is a flowchart illustrating an exemplary process for generating a trained image processing model according to some embodiments of the present disclosure.

FIG. 8 is a flowchart illustrating an exemplary process for generating a trained image processing model according to some embodiments of the present disclosure. In some embodiments, a process 800 may be implemented as a set of instructions (e.g., an application) stored in the storage device 150, the storage 220, or the storage 390. The processing device 140B (e.g., implemented on the processing device 140, the processor 210, the CPU 340, one or more modules illustrated in FIG. 4B, or an external device of the image processing device 100) may execute the set of instructions, and when executing the instructions, the processing device 140B may be configured to perform the process 800. The operations of the illustrated process 800 presented below are intended to be illustrative. In some embodiments, the process 800 may be accomplished with one or more additional operations not described, and/or without one or more of the operations discussed. Additionally, the order of the operations of the process 800 illustrated in FIG. 8 and described below is not intended to be limiting. In some embodiments, one or more operations of the process 800 may be performed to achieve at least part of operation 620 as described in connection with FIG. 6. In some embodiments, the process 800 may be performed by another device or system other than the image processing system 100, e.g., a device or system of a vendor of a manufacturer.

In 805, the processing device 140B (e.g., the acquisition module 430) may obtain a preliminary model. In some embodiments, the preliminary model may include an FB-CNN as described in connection with FIG. 9 and/or FIG. 10.

In some embodiments, the processing device 140B may perform a training process including a plurality of iterations to iteratively update one or more parameter values of the preliminary model. In some embodiments, the training process may include a first training process and a second training process. The first training process may include multiple first iterations, and the second training process may include multiple second iterations.

In 810, the processing device 140B (e.g., the acquisition module 440) may obtain training samples.

The training samples may include a plurality of sample first images generated based on a first tracer, a plurality of reference first images each of which corresponds to one of the plurality of sample first images and has a higher image quality than the corresponding sample first image, a plurality of sample second images generated based on a second tracer different from the first tracer, and a plurality of reference second images each of which corresponds to one of the plurality of sample second images and has a higher image quality than the corresponding sample second image.

In 820, the processing device 140B (e.g., the model determination module 440) may generate (or update) at least one first prediction output based on at least one sample first image and the (updated) preliminary model.

The processing device 140B may input the at least one sample first image into the preliminary model at the beginning of the multiple first iterations, or an updated preliminary model generated in a previous first iteration. The (updated) preliminary model may output the at least one first prediction output. For example, during an iteration of the multiple first iterations, the processing device 140B may input the at least one sample first image of the training samples into the preliminary (or updated) model. The preliminary (or updated) model may output at least one first prediction output each of which corresponds to one of the at least one sample first image. In next iteration, the processing device 140B may also input the at least one sample first image of the training samples into the model updated in the previous iteration. The updated model may output at least one new (or updated) prediction output each of which corresponds to one of the at least one sample first image. As another example, the training samples may be divided into several groups each of which includes at least one first training sample set. During an iteration of the multiple first iterations, the processing device 140B may input the sample first image(s) in one group of the training samples into the preliminary (or updated) model. The preliminary (or updated) model may output the corresponding first prediction output(s) each of which corresponds to one sample first image of the group. In next iteration, the processing device 140B may input the sample first image(s) in another group of the training samples into the model updated in the previous iteration. The updated model may output the corresponding first prediction output(s) each of which corresponds to one sample first image of another group.

In 830, the processing device 140B (e.g., the model determination module 440) may determine whether a first condition is satisfied.

The first condition may be similar to the termination condition as described in operation 620. For example, the first condition may relate to a first loss function or a first iteration count of the multiple first iterations (or first training process). Merely by way of example, a value of the first loss function may be generated at least based on the reference first images and the first prediction outputs. As another example, the first condition may be satisfied if the value of the first loss function associated with the preliminary model is minimal or smaller than a threshold (e.g., a constant). As still an example, the first condition may be satisfied when a specified number (or count) of iterations are performed in the first training process.

In response to determining that the first condition is not satisfied, the processing device 140B may update one or more parameters of the preliminary model and execute the process 800 to return operation 820 to update the at least one first prediction output based on the at least one sample first image and the updated model. In response to determining that the first condition is satisfied, the processing device 140B may designate the preliminary or updated model as a second intermediate model in operation 840. In other words, the preliminary model may be trained to generate the second intermediate model using the plurality of sample first images and the plurality of reference first images in the first training process.

In 850, the processing device 140B (e.g., the model determination module 440) may generate (or update) at least one second prediction output based on at least one sample second image and the (updated) second intermediate model.

The processing device 140B may input the at least one sample second image into the second intermediate model at the beginning of the multiple second iterations, or an updated second intermediate model generated in a previous second iteration. The (updated) second intermediate model may output the at least one second prediction output. For example, during an iteration of the multiple second iterations, the processing device 140B may input the at least one sample second image of the training sample into the (updated) second intermediate model. The (updated) second intermediate model may output at least one second prediction output each of which corresponds to one of the at least one sample second image. In next iteration, the processing device 140B may also input the at least one sample second image of the training samples into the model updated in the previous iteration. The updated model may output at least one new (or updated) prediction output each of which corresponds to one of the at least one sample second image. As another example, the training samples may be divided into several groups each of which includes at least one second training sample set. During an iteration of the multiple second iterations, the processing device 140B may input the sample second image(s) in one group of the training samples into the (updated) second intermediate model. The (updated) second intermediate model may output the corresponding second prediction output(s) each of which corresponds to one sample second image of the group. In next iteration, the processing device 140B may input the sample second image(s) in another group of the training samples into the model updated in the previous iteration. The updated model may output the corresponding second prediction output(s) each of which corresponds to one sample second image of another group.

In 860, the processing device 140B (e.g., the model determination module 440) may determine whether a second condition is satisfied.

The second condition may be the same as or different from the first condition. For example, the second condition may relate to a second loss function or a second iteration count of the multiple second iterations (or second training process). As another example, the second condition may be satisfied when a specified number (or count) of iterations are performed in the second training process.

In response to a determination that the second condition is not satisfied, the processing device 140B may execute the process 800 to return operation 840 to update the second intermediate model. In some embodiments, the processing device 140B may iteratively update parameter values of preset layers in the second intermediate model based on the plurality of sample second images and the plurality of reference second images, and fix parameters in the second intermediate model other than the parameters of the preset layers. In some embodiments, there are a threshold count (e.g., 0, 1, 2, 3, 4, 5, etc.) of layers between the preset layers and an output layer of the second intermediate model.

In response to a determination that the second condition is satisfied, the processing device 140B may designate the (updated) second intermediate model as a trained image processing model in operation 870. In other words, the second intermediate model may be trained to generate the trained image processing model using the plurality of sample second images and the plurality of reference second images in the second training process.

According to the process 800, the trained image processing model is trained using sample data corresponding to the first tracer and the second tracer. If the second tracer is not commonly used (i.e., training data corresponding to the second tracer is few), the trained image processing model corresponding to the second tracer may still be generated due to the participation of a large amount of sample data corresponding to the first tracer in the first training process, that is, the trained image processing model trained using sample data corresponding to the first tracer and the second tracer can be used to process images generated based on the second tracer.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140B may update the trained image processing model at a certain time interval (e.g., per month, per two months) based on a plurality of newly obtained scanning records.

Figure 9:
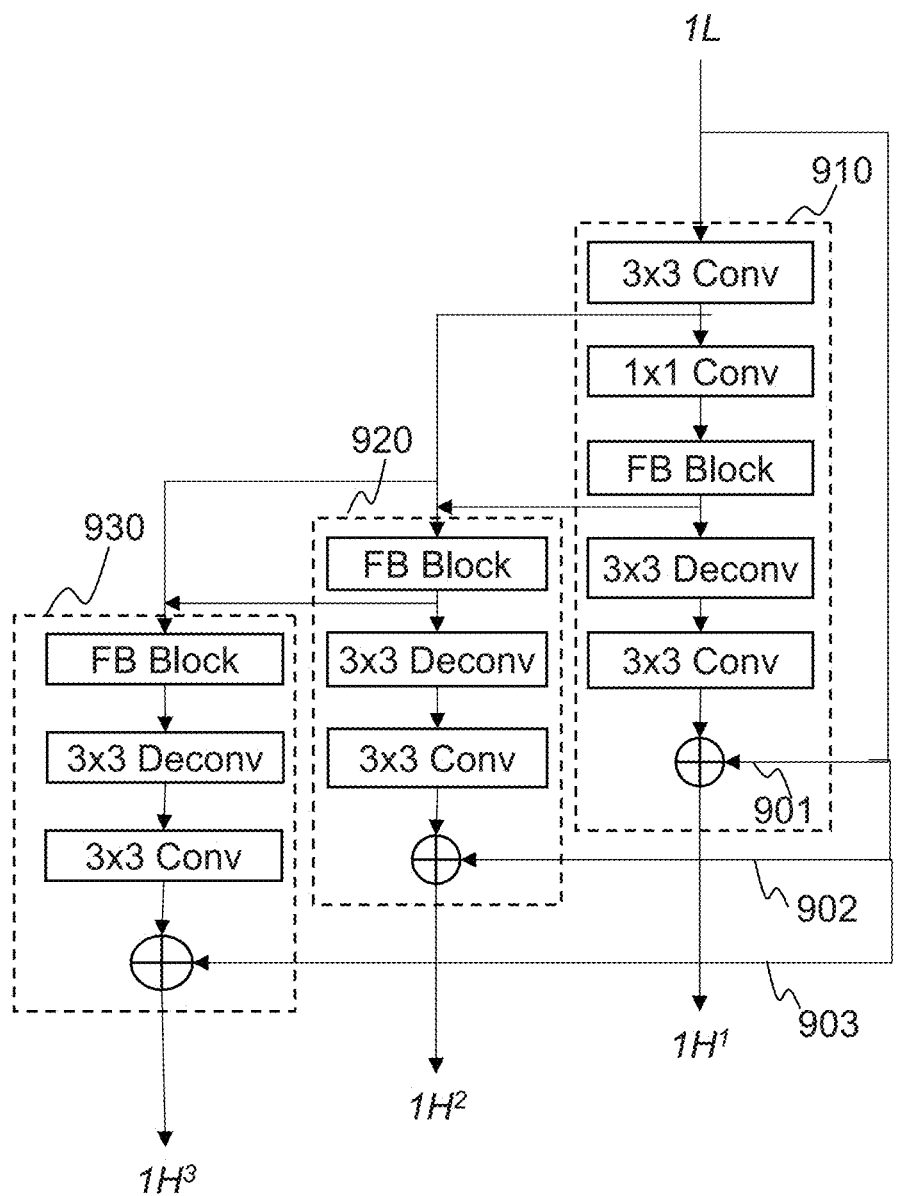
FIG. 9 is a schematic diagram illustrating a network structure of a trained image processing model according to some embodiments of the present disclosure.

FIG. 9 is a schematic diagram illustrating a network structure of a trained image processing model according to some embodiments of the present disclosure.

In some embodiments, a trained image processing model may be a trained Feedback Convolutional Neural Network (FB-CNN) including a plurality of sequentially connected subnets. For example, as illustrated in FIG. 9, an FB-CNN 900 (also referred to as a model 900 for brevity) may include three subnets (e.g., a first subnet 910, a second subnet 920, a third subnet 930). In some embodiments, 1L may be an input of the model 900, and $1H^1$, $1H^2$, and $1H^3$ may be outputs of the first subnet 910, the second subnet 920, and the third subnet 930, respectively. The output (e.g., $1H^3$) of the last subnet (e.g., the third subnet 930) of the model 900 may be the final output of the model 900.

In some embodiments, the input (e.g., the 1L) of the model 900 may be connected to an output of each of the plurality of subnets by a first connection component. For example, solid lines 901, 902, and 903 illustrated in FIG. 9 may represent the first connection component between the input and output of the first subnet 910, the second subnet 920, and the third subnet 930, respectively. Merely by way of example, the first connection component may include a residual connection. The first connection component may establish shortcuts to jump over one or more layers of the model 900 so as to solve the problem of a vanishing gradient and improve the efficiency of the training process of the model 900.

In some embodiments, each of the plurality of subnets may include at least one convolution block, at least one deconvolution block, and a feedback block (FB-block). In some embodiments, a convolution block may be a convolution layer, for example, a 3×3 convolution layer, a 1×1 convolution layer. A deconvolution block may be a deconvolution layer, for example, a 3×3 deconvolution layer. For example, as illustrated in FIG. 9, the first subnet 910 may include two 3×3 convolution layers, a 1×1 convolution layer, and a 3×3 deconvolution layer. The second subnet 920 or the third subnet 930 may include a 3×3 convolution layer and a 3×3 deconvolution layer. In some embodiments, the convolution layer(s) and/or the deconvolution layer(s) may include an activation function, such as a PReLU function, a ReLU function, etc. In some embodiments, an output of the FB-block in a subnet may be inputted into a next subnet connected to the subnet.

Figure 10:
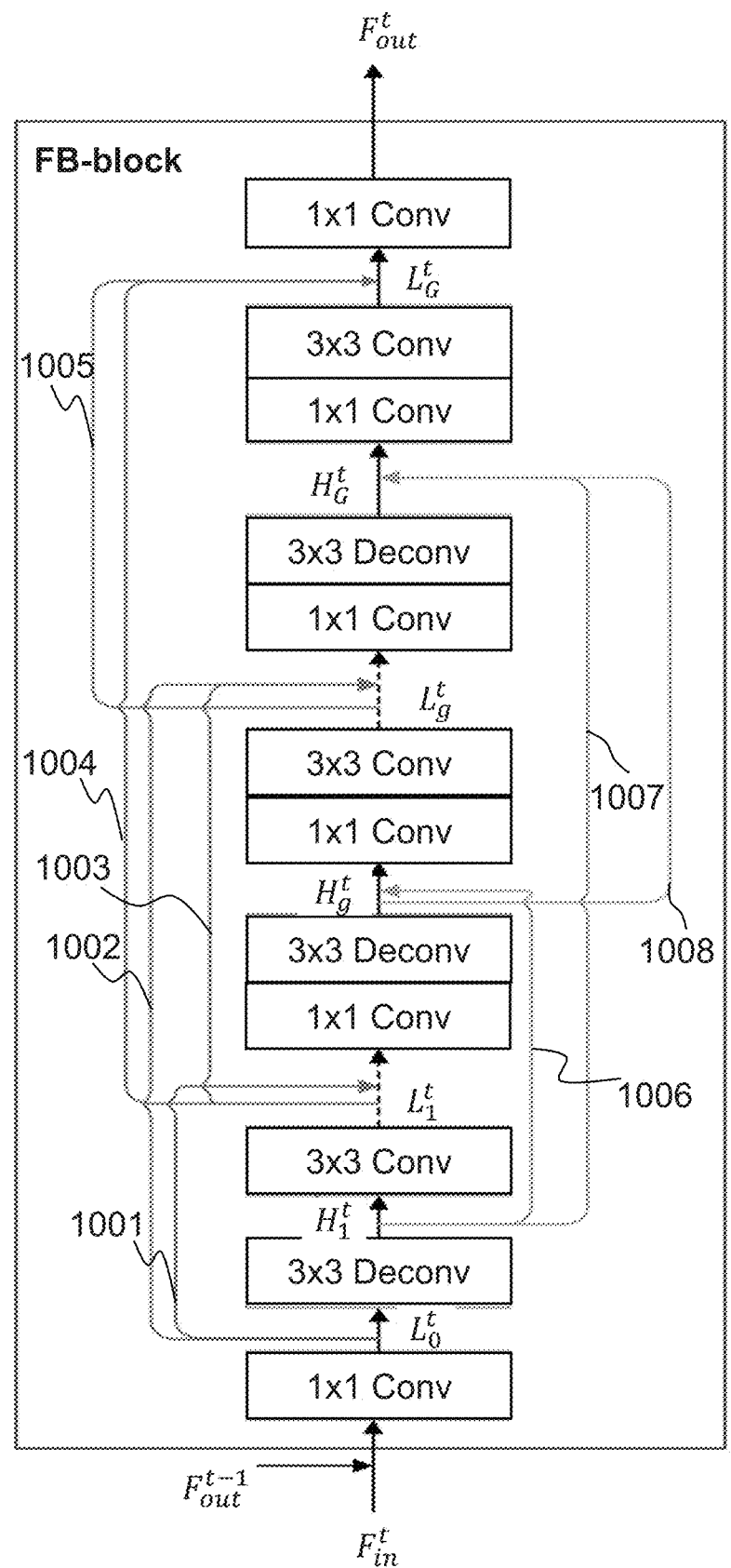
FIG. 10 is a schematic diagram illustrating a structure of a feedback block according to some embodiments of the present disclosure.

FIG. 10 is a schematic diagram illustrating a structure of a feedback-block according to some embodiments of the present disclosure. As illustrated in FIG. 10, a FB-block may include a plurality of convolution layers and deconvolution layers. The convolution layers may reduce a count of feature maps and accelerate an inference process of the model 900. A portion of the plurality of convolution layers and deconvolution layers may form projection groups each of which includes paired convolution layer and deconvolution layer. Different layers in at least part of the plurality of convolution layers and deconvolution layers may be connected via a second connection component (e.g., second connections 1001-1008). The second connection component may include a dense connection. The FB-block may enrich the expression of high-level features through the second connection components in the FB-block. The second connection components may make the transmission of gradients and features more effective and reduce a count of parameters of the model 900. The second connection components may facilitate concatenation of features of different convolution layers.

The 3×3 convolution layers (also referred to as 3×3 Conv) shown in FIG. 9 and FIG. 10 denote convolution layers having kernel sizes of 3×3 pixels. The 1×1 convolution layers (also referred to as 1×1 Conv) shown in FIG. 9 and FIG. 10 denote convolution layers having kernel sizes of 1×1 pixel. The 3×3 convolution layers and 1×1 convolution layers may extract features of input data. The 3×3 deconvolution layers (also referred to as 3×3 Deconv) shown in FIG. 9 and FIG. 10 denote deconvolution layers having kernel sizes of 3×3 pixels. $F_{out}^{t-1}$ (shown in FIG. 10) represents a high-level feature after a (t−1)-th subnet, which may serve as feedback information to guide a low-level feature expression $F_{in}^{t}$ (shown in FIG. 10) of a t-th subnet and enable a learning and expression capability of the model 900 to enhance gradually. t may be 1, 2, or 3. As used herein, a high-level feature may refer to information at a large scale. Exemplary high-level features may include semantic information, etc. A low-level feature may refer to information at a small scale. Exemplary low-level features may include texture, an edge, etc. $L_0^{t}$, $L_1^{t}$, $L_g^{t}$, and $L_G^{t}$ (shown in FIG. 10) representing low-level features, respectively. $H_1^{t}$, $H_g^{t}$, and $H_G^{t}$ (shown in FIG. 10) represent high-level features, respectively. Each of the three subnets of the model 900 may share same weights, which may greatly compress a size of the model 900 and reduce a training time of the model 900.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures, or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer-readable program code embodied thereon.

A non-transitory computer-readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer-readable signal medium may be any computer-readable medium that is not a computer-readable storage medium and that may communicate, propagate, or transport a program for use by or in connection with an instruction execution system, apparatus, or device. Program code embodied on a computer-readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python, or the like, conventional procedural programming languages, such as the "C" programming language, Visual Basic, Fortran, Perl, COBOL, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, e.g., an installation on an existing server or mobile device.

Similarly, it should be appreciated that in the foregoing description of embodiments of the present disclosure, various features are sometimes grouped together in a single embodiment, figure, or description thereof to streamline the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate" or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system, comprising:
   at least one storage device storing executable instructions for model training; and
   at least one processor in communication with the at least one storage device, wherein when executing the executable instructions, the at least one processor is configured to cause the system to perform operations including:
   obtaining training samples, the training samples including at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image; and
   generating a trained image processing model by training a preliminary model using the training samples.

2. The system of claim 1, wherein obtaining the training samples includes:
   obtaining one of the at least one reference first image generated based on first imaging data acquired by an imaging device according to the first tracer;
   generating the corresponding sample first image by down-sampling the first imaging data;
   obtaining one of the at least one reference second image generated based on second imaging data acquired by the imaging device according to the second tracer; and
   generating the corresponding sample second image by down-sampling the second imaging data.

3. The system of claim 1, wherein a first count of the at least one sample first image or the at least one reference first image is greater than a second count of the at least one sample second image or the at least one reference second image.

4. The system of claim 1, wherein generating the trained image processing model by training the preliminary model using the training samples includes:
   for each of the at least one sample first image, obtaining a first preliminary weight;
   for each of the at least one sample second image, obtaining a second preliminary weight;
   determining a loss function based on the at least one first preliminary weight and the at least one second preliminary weight; and
   generating the trained image processing model by training the preliminary model based on the loss function.

5. The system of claim 4, wherein the loss function includes a first term at least related to the at least one first preliminary weight and a second term at least related to the at least one second preliminary weight.

6. The system of claim 4, wherein the at least one second preliminary weight is greater than the at least one first preliminary weight.

7. The system of claim 4, wherein the training process includes a plurality of iterations, at least one iteration of the plurality of iterations including:
  determining at least one first prediction output by inputting the at least one sample first image into a first intermediate model, the first intermediate model being the preliminary model in the first iteration of the plurality of iterations, or an updated model generated in a previous iteration;
  determining at least one second prediction output by inputting the at least one sample second image into the first intermediate model;
  obtaining at least one first current weight corresponding to the at least one sample first image, and at least one second current weight corresponding to the at least one sample second image, the at least one first current weight being the at least one first preliminary weight in the first iteration of the plurality of iterations, or at least one updated weight corresponding to the at least one first preliminary weight in the previous iteration, the at least one second current weight being the at least one second preliminary weight in the first iteration of the plurality of iterations, or at least one updated weight corresponding to the at least one second preliminary weight in the previous iteration;
  determining a value of the loss function based on the at least one first current weight, the at least one second current weight, the at least one first prediction output, the at least one reference first image, the at least one second prediction output, and the at least one reference second image; and
  updating at least one parameter of the first intermediate model based on the value of the loss function.

8. The system of claim 7, wherein the at least one iteration of the plurality of iterations further includes:
  determining a current image difference between the at least one reference second image and the at least one second prediction output; and
  updating the at least one first current weight and the at least one second current weight based on the current image difference.

9. The system of claim 8, wherein determining the current image difference between the at least one reference second image and the at least one second prediction output includes:
  determining pixel differences between a plurality of pixels of each of the at least one reference second image and a plurality of pixels of each of the at least one second prediction output; and
  determining the current image difference based on the pixel differences and the at least one second current weight.

10. The system of claim 8, wherein updating the at least one first current weight and the at least one second current weight based on the current image difference includes:
  obtaining an initial factor;
  determining a target factor by comparing the current image difference of the current iteration and a previous image difference that corresponds to the current image difference and is determined in the previous iteration; and
  updating the at least one first current weight and the at least one second current weight based on the comparison.

11. The system of claim 10, wherein updating the at least one first current weight and the at least one second current weight based on the comparison includes:
  in response to determining that the current image difference is greater than the previous image difference, decreasing the at least one first current weight; and increasing the at least one second current weight.

12. The system of claim 10, wherein updating the at least one first current weight and the at least one second current weight based on the comparison includes:
  in response to determining that the current image difference is less than the previous image difference, increasing the at least one first current weight; and decreasing the at least one second current weight.

13. The system of claim 1, wherein generating the trained image processing model by training the preliminary model using the training samples includes:
  generating a second intermediate model by training the preliminary model using the at least one sample first image and the at least one reference first image; and
  generating the trained image processing model by training the second intermediate model using the at least one sample second image and the at least one reference second image.

14. The system of claim 13, wherein generating the trained image processing model by training the second intermediate model using the at least one sample second image and the at least one reference second image includes:
  generating the trained image processing model by iteratively updating parameter values of preset layers in the second intermediate model based on the at least one sample second image and the at least one reference second image.

15. The system of claim 14, wherein there are a threshold count of layers between the preset layers and an output layer of the second intermediate model, and the threshold count of layers is less than 3.

16. The system of claim 1, wherein
  the trained image processing model is a trained Feedback Convolutional Neural Network (FB-CNN) including a plurality of sequentially connected subnets, and
  an input of the FB-CNN is connected to an output of each of the plurality of subnets.

17. The system of claim 16, wherein
  each of the plurality of subnets includes at least one convolution block, at least one deconvolution block, and a feedback block (FB-block), an output of the FB-block in the subnet being inputted into a next subnet connected to the subnet,
  the FB-block includes a plurality of convolutional layers and deconvolutional layers, a portion of the plurality of convolutional layers and deconvolutional layers being interleaved, and
  different layers in at least part of the plurality of convolutional layers and deconvolutional layers are connected to each other.

18. The system of claim 1, wherein
  the at least one sample first image and the at least one sample second image serve as inputs for training the preliminary model, and
  the at least one reference first image and the at least one reference second image serve as reference outputs for training the preliminary model.

19. A system, comprising:
at least one storage device storing executable instructions for image processing; and
at least one processor in communication with the at least one storage device, wherein when executing the executable instructions, the at least one processor is configured to cause the system to perform operations including:
- obtaining an initial image of a subject acquired by an imaging device according to a second tracer;
- obtaining a trained image processing model; and
- generating a target image by inputting the initial image into the trained image processing model, the target image having a higher image quality than the initial image;
- wherein the trained image processing model is provided by training a preliminary model using training samples, the training samples including at least one sample first image generated based on a first tracer, at least one reference first image each of which corresponds to one of the at least one sample first image and has a higher image quality than the corresponding sample first image, at least one sample second image generated based on the second tracer different from the first tracer, and at least one reference second image each of which corresponds to one of the at least one sample second image and has a higher image quality than the corresponding sample second image.

20. A method for model training, implemented on a computing device having at least one processor and at least one storage device, the method comprising:
- obtaining training samples, the training samples including at least one sample first image generated based on a first tracer, at least one reference first image each of which corresponds to one of the at least one sample first image and has a higher image quality than the corresponding sample first image, at least one sample second image generated based on a second tracer different from the first tracer, and at least one reference second image each of which corresponds to one of the at least one sample second images and has a higher image quality than the corresponding sample second image; and
- generating a trained image processing model by training a preliminary model using the training samples.

* * * * *